US006177086B1

(12) United States Patent
Riley et al.

(10) Patent No.: US 6,177,086 B1
(45) Date of Patent: Jan. 23, 2001

(54) **DNA MOLECULE CONFERRING ON *MYCOBACTERIUM TUBERCULOSIS* RESISTANCE AGAINST ANTIMICROBIAL REACTIVE OXYGEN AND NITROGEN INTERMEDIATES**

(75) Inventors: Lee W. Riley, Berkeley, CA (US); Carl F. Nathan, Larchmont, NY (US); Sabine Ehrt, Berkeley, CA (US)

(73) Assignee: Cornell Research Foundation, Inc., Ithaca, NY (US)

( * ) Notice: Under 35 U.S.C. 154(b), the term of this patent shall be extended for 0 days.

(21) Appl. No.: 09/067,626

(22) Filed: Apr. 28, 1998

Related U.S. Application Data

(60) Provisional application No. 60/045,688, filed on May 6, 1997.

(51) Int. Cl.[7] .......................... A61K 39/04; A61K 39/02; C12P 21/06; C12P 21/04; C12N 1/20

(52) U.S. Cl. .................................... 424/248.1; 424/234.1; 435/69.1; 435/70.1; 435/170; 435/253.1

(58) Field of Search ............................. 424/248.1, 234.1; 435/69.1, 70.1, 170, 253.1

(56) References Cited

U.S. PATENT DOCUMENTS

| | | | |
|---|---|---|---|
| 4,237,224 * | 12/1980 | Cohen et al. .......................... | 435/68 |
| 5,108,745 | 4/1992 | Horwitz . | |
| 5,183,737 | 2/1993 | Crawford et al. . | |
| 5,239,066 | 8/1993 | Falkow et al. . | |

FOREIGN PATENT DOCUMENTS

| | | |
|---|---|---|
| WO 95/06726 | 3/1995 | (EP) . |

OTHER PUBLICATIONS

Roberts et al, "Maximizing gene expression on a plasmid using recombination in vitro", Methods in Enzymology, vol. 68, pp. 473–482, Jan. 1, 1979.*

GenBank, Accession No. P95301, direct submission, Sep. 1, 1996.*

Horwitz, et al., "Protective Immunity Against Tuberculosis Induced by Vaccination with Major Extracellular Proteins of *Mycobacterium tuberculosis,*" *Proc. Natl. Acad. Sci. USA*, 92:1530–1534 (1995).

Isberg, et al., "A Single Genetic Locus Encoded by *Yersinia pseudotuberculosis* Permits Invasion of Cultured Animal Cells by *Escherichia coli* K–12," *Nature*, 317:262–264 (1985).

Arruda, et al., "Cloning of a *Mycobacterium tuberculosis* Gene Necessary for Invation of Cultured Epithelial Cells," *Abstracts of the General Meeting*, 92:41 (1992).

Bloom, et al., "Tuberculosis: Commentary on a Reemergent Killer," *Science*, 257:1055–1064 (1992).

Ten Basics on the Diagnosis, Treatment, and Prevention of Tuberculosis, *City Health Information*, 11(5) (1992).

"Control of Tuberculosis in the United States," *American Thoracic Society*, 146:1623–1633 (1992).

Laraque, et al., "Tuberculosis in HIV–Infected–Patients," *The AIDS Reader*, pp. 171–180 (Sep./Oct. 1992).

Arruda, et al., "Cloning of an *M. tuberculosis* DNA Fragment Associated with Entry and Survival Inside Cells," *Science*, 261:1454–1457 (1993).

Kuo, et al., "Novel Systems for Controlled Delivery of Macromolecules," *Critical Reviews in Eukaryotic Gene Expression*, 6(1):59–73 (1996).

Ledley, F.D., "Nonviral Gene Therapy: The Promise of Genes as Pharmaceutical Products," *Human Gene Therapy*, 6:1129–1144 (1995).

Stoeckle, et al., "Catalase–Peroxidase Gene Sequences in Isoniazid–Sensitive and –Resistant Strains of *Mycobacterium Tuberculosis* from New York City," *The Journal of Infectious Diseases*, 168:1063–1065 (1993).

Zhang, et al., "Molecular Mechanisms of Isoniazid: A Drug at the Front Line of Tuberculosis Control," *Trends Microbiol,* 1(3):109–113 (1993).

Ferrazoli, et al., "Catalase Expression, katG, and MIC of Isoniazid for *Mycobacterium tuberculosis* Isolates from São Paulo,Brazil," *The Journal of Infectious Diseases*, 171:237–240 (1995).

Banerjee, et al., "inhA, a Gene Encoding a Target for Isoniazid and Ethionamide in *Mycobacterium tuberculosis,*" *Science*, 263:227–230 (1994).

Mdluli, et al., "Biochemical and Genetic Data Suggest That InhA is Not the Primary Target for Activated Isoniazid in *Mycobacterium tuberculosis,*" *The Journal of Infectious Diseases*, 174:1085–1090 (1996).

Ehrt, et al., "Resistance to Reactive Nitrogen Intermediates by *Mycobacterium tuberculosis,*" *J. Cellular Biochemistry*, Supplement 19B:83 (1995).

Lowenstein, et al., "Nitric Oxide: A Physiologic Messenger," *Ann. Intern. Med.*, 120:227–237 (1994).

Stamler, et al., "Biochemistry of Nitric Oxide and Its Redox––Activated Forms," *Science*, 258:1898–1902 (1992).

Doi, et al., "Resistance to Nitric Oxide in *Mycobacterium avium* Complex and Its Implication in Pathogenesis," *Infection and Immunity*, 61(5):1980–1989 (1993).

(List continued on next page.)

*Primary Examiner*—Rodney P. Swart
(74) *Attorney, Agent, or Firm*—Nixon Peabody LLP

(57) ABSTRACT

The present invention relates to a DNA molecule conferring on Mycobacterium tuberculosis resistance to antimicrobial reactive oxygen intermediates and reactive nitrogen intermediates. The protein encoded by this DNA molecule is useful in vaccines to prevent invention by Mycobacterium tuberculosis, while the antibodies raised against this protein can be employed in passively immunizing those already infected by the organism. Both these proteins and antibodies may be utilized in diagnostic assays to detect Mycobacterium tuberculosis in tissue or bodily fluids. The protein or polypeptide is also useful as a therapeutic in treating conditions mediated by the production of reactive oxygen intermediates and nitrogen intermediates.

9 Claims, 12 Drawing Sheets

OTHER PUBLICATIONS

Flesch, et al., "Mechanisms Involved in Mycobacterial Growth Inhibition by Gamma Interferon–Activated Bone Marrow Macrophages: Role of Reactive Nitrogen Intermediates," *Infection and Immunity*, 59(9):3213–3218 (1991).

Schneemann, et al., "Nitric Oxide Synthase Is Not a Constituent of the Antimicrobial Armature of Human Mononuclear Phagocytes," *The Journal of Infectious Diseases*, 167:1358–1363 (1993).

Lane, et al., "Expression of Inducible Nitric Oxide Synthase by Stimulated Macrophages Correlatess With Their Antihistoplasma Activity," *Infection and Immunity*, 62(4):1478–1479 (1994).

Flesch, et al., "Mycobacterial Growth Inhibition by Interferon–γ–Activated Bone Marrow Macrophages and Differential Susceptibility Among Strains of *Mycobacterium tuberculosis*," *The Journal of Immunology*, 138(12):4408–4413 (1987).

Kobzik, et al., "Nitric Oxide Synthase in Human and Rat Lung: Immunocytochemical and Histochemical Localization," *Am. J. Respir. Cell Mol. Biol.*, 9:371–377 (1993).

Nathan, "Natural Resistance and Nitric Oxide," *Cell*, 82:873–876 (1995).

Ehrt et al., "A Novel Antioxidant Gene from *Mycobacterium tuberculosis*," *J. Exp. Med.*, 186(11):1885–1896 (1997).

Database GENBANK on MPSRCH, PCT/US98/08497–3, Ehrt et al., Direct Submission, Commercial Sequence Databases MB154 and GENBANK106. Accession No. Y08323, Dec. 15, 1996.

Database GENBANK on MPSRCH, PCT/US98/08497–2, Ehrt et al., Nitric Oxide Resistance Protein, Commercial Sequence Database sptrembl5. Accession No. P95301, May 1, 1997.

* cited by examiner

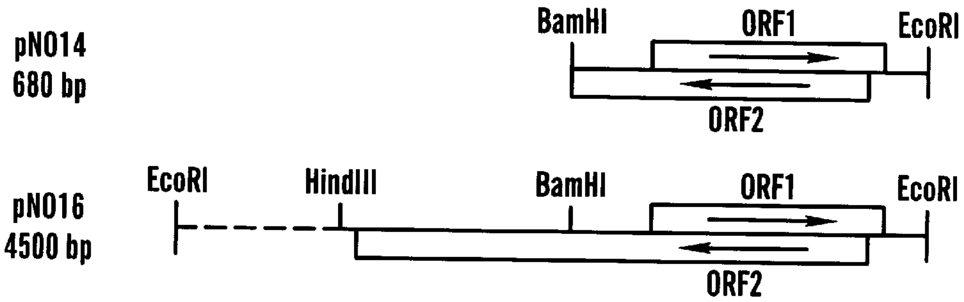

*FIG. 2B*

```
GGATCCGACCACGGGATCTCGTCGCTGAGCACGAAGTCCACCTTGGCGATGCCAGCGCGA   60
AATCGATAGCGGCGCAATGCTTTGGCATACCGATGTGGAAGCTTGTCGCGGTAAACCCGC   120
AGCAGGGCGGTGGGTGCGGTGTCGAAGACGACCACACTTCTTTGCGGTTCGGTGATCTCG   180
         V  G  A  V  S  K  T  T  T  L  L  C  G  S  V  I  S
ACACCGGCCGCGAGCCGACCACCATGCGCGCGTAGATCGGCGATCAGCGCGTCGGCTATC   240
T  P  A  A  S  R  P  P  C  A  R  R  S  A  I  S  A  S  A  I
GCCTGGGTGCCGCCCACCGGAATCGGCCAGCCGACCGAATGGGCCAGCGTTGCCAGCATC   300
A  W  V  P  P  T  G  I  G  Q  P  T  E  W  A  S  V  A  S  I
AGTCCGGCGCCGGCCGACACCAGTGACGGCAACGGTGAAATCGCGTGGGCGGCAACGCCG   360
S  P  A  P  A  D  T  S  D  G  N  G  E  I  A  W  A  A  T  P
GTGAACAACGCGCGGGCATCCTCGCCCGCCAGCGACCGCCAGGCAGGGGTGCCCTGGGCC   420
V  N  N  A  R  A  S  S  P  A  S  D  R  Q  A  G  V  P  W  A
AGCATCCGCAGCCCGAGACGCAGGACCGAGCCCAGTGCAGTAGGCAAAGACCGCTTGTCG   480
S  I  R  S  P  R  R  R  T  E  P  S  A  V  G  K  D  R  L  S
GAGAGCATGAACTCCACGACCGTCTCCGAGTGCGCCACCAACCGGCCCAGCAGGCGCCGC   540
E  S  M  N  S  T  T  V  S  E  C  A  T  N  G  P  S  R  R  R
CAGGACGCGCCGTCGTCCAGCTTGGCGCAGGTGTGCGCCAGATCGTGATAGGCGATCGCC   600
Q  D  A  P  S  S  S  L  A  Q  V  C  A  R  S  .
GCGGGCCGCCCGGGTAGCGGGTTGGCGTAGGCGATGTCGGGCACGGTCAGCGTCACTCCG   660
CGCGCGGGTAGGTCGAATTC   680
```

*FIG. 2C*

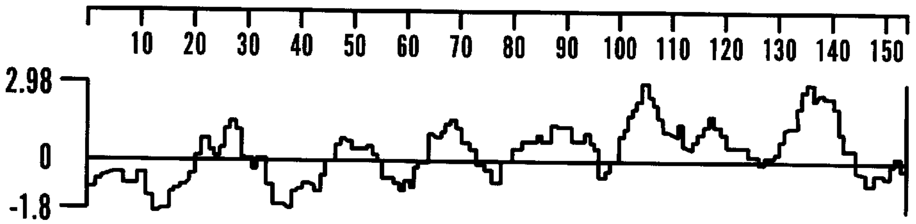

*FIG. 2D*

SEQUENCE LISTING

```
(1) GENERAL INFORMATION:

   (iii) NUMBER OF SEQUENCES: 13


(2) INFORMATION FOR SEQ ID NO:1:

     (i) SEQUENCE CHARACTERISTICS:
          (A) LENGTH: 1244 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:1:

AAGCTTCGTT ATGGCCTCAG CTCATGGCCC AAAGGGGGCA TGCGGGTGAT GCCGAACTCG      60

GTGCGCAACA GCGTTCGAGC GGCATACCAG CCGCACATGC CGTGCACGCC GGCGCCGGGC     120
```

-continued

```
GGAGTCGCCG CAGAACACAG GTACACCTTG GGAATCGGTG TGCGCCAGGG ATTCAACCGC     180

GGGGTGGGGC CGGCGATCGC GCGCCAGGTC GAGTTGGCGC CGACCGTGAT GTCACCGCCG     240

ACGTAGTTGG CGTTGTGGTC GGCCATCCGC GCGGCGGGCA CGGCGCGGCC CGCCACCACG     300

ATGTCACGGA AGCCGGGGGC GAACCGCTCG AGGACGCTGG TTACGGTCTC GGTCGCGTCG     360

AGCGTGGACC CCGACGGCAC GTGGGCATAG GTCCAGAACG GACGGCGGCC GGTTTCGTCG     420

ATGCGGCCGG GGTCGGCGAC GTGCGGACAC GCGGCCAGCA CCATCGGCCA GTCGGCGTGG     480

CGTCCCGCCG CGACGTCTGC CTCGGCGCGC GCCATCTGGT CACGGGTGCC GCCGAGATGC     540

AGGGTCGCAG CCCGCCGCAG CCGCGGATCC GACCACGGGA TCTCGTCGCT GAGCACGAAG     600

TCCACCTTGG CGATGCCAGC GCGAAATCGA TAGCGGCGCA ATGCTTTGGC ATACCGATGT     660

GGAAGCTTGT CGCGGTAAAC CCGCAGCAGG GCGGTGGGTG CGGTGTCGAA GACGACCACA     720

CTTCTTTGCG GTTCGGTGAT CTCGACACCG GCCGCGAGCC GACCACCATG CGCGCGTAGA     780

TCGGCGATCA GCGCGTCGGC TATCGCCTGG GTGCCGCCCA CCGGAATCGG CCAGCCGACC     840

GAATGGGCCA GCGTTGCCAG CATCAGTCCG GCGCCGGCCG ACACCAGTGA CGGCAACGGT     900

GAAATCGCGT GGGCGGCAAC GCCGGTGAAC AACGCGCGGG CATCCTCGCC CGCCAGCGAC     960

CGCCAGGCAG GGGTGCCCTG GGCCAGCATC CGCAGCCCGA GACGCAGGAC CGAGCCCAGT    1020

GCAGTAGGCA AAGACCGCTT GTCGGAGAGC ATGAACTCCA CGACCGTCTC CGAGTGCGCC    1080

ACCAACGGGC CCAGCAGGCG CCGCCAGGAC GCGCCGTCGT CCAGCTTGGC GCAGGTGTGC    1140

GCCAGATCGT GATAGGCGAT CGCCGCGGGC CGCCCGGGTA GCGGGTTGGC GTAGGCGATG    1200

TCGGGCACGG TCAGCGTCAC TCCGCGCGCG GGTAGGTCGA ATTC                     1244
```

(2) INFORMATION FOR SEQ ID NO:2:

(i) SEQUENCE CHARACTERISTICS:
(A) LENGTH: 152 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:2:

```
Val Gly Ala Val Ser Lys Thr Thr Thr Leu Leu Cys Gly Ser Val Ile
1               5                   10                  15

Ser Thr Pro Ala Ala Ser Arg Pro Pro Cys Ala Arg Arg Ser Ala Ile
            20                  25                  30

Ser Ala Ser Ala Ile Ala Trp Val Pro Pro Thr Gly Ile Gly Gln Pro
        35                  40                  45

Thr Glu Trp Ala Ser Val Ala Ser Ile Ser Pro Ala Pro Ala Asp Thr
    50                  55                  60

Ser Asp Gly Asn Gly Glu Ile Ala Trp Ala Ala Thr Pro Val Asn Asn
65                  70                  75                  80

Ala Arg Ala Ser Ser Pro Ala Ser Asp Arg Gln Ala Gly Val Pro Trp
                85                  90                  95

Ala Ser Ile Arg Ser Pro Arg Arg Arg Thr Glu Pro Ser Ala Val Gly
            100                 105                 110

Lys Asp Arg Leu Ser Glu Ser Met Asn Ser Thr Thr Val Ser Glu Cys
        115                 120                 125

Ala Thr Asn Gly Pro Ser Arg Arg Arg Gln Asp Ala Pro Ser Ser Ser
    130                 135                 140
```

-continued

Leu Ala Gln Val Cys Ala Arg Ser
145 150

(2) INFORMATION FOR SEQ ID NO:3:

(i) SEQUENCE CHARACTERISTICS:
(A) LENGTH: 1244 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

GAATTCGACC TACCCGCGCG CGGAGTGACG CTGACCGTGC CCGACATCGC CTACGCCAAC 60

CCGCTACCCG GGCGGCCCGC GGCGATCGCC TATCACGATC TGGCGCACAC CTGCGCCAAG 120

CTGGACGACG GCGCGTCCTG GCGGCGCCTG CTGGGCCCGT TGGTGGCGCA CTCGGAGACG 180

GTCGTGGAGT TCATGCTCTC CGACAAGCGG TCTTTGCCTA CTGCACTGGG CTCGGTCCTG 240

CGTCTCGGGC TGCGGATGCT GGCCCAGGGC ACCCCTGCCT GGCGGTCGCT GGCGGGCGAG 300

GATGCCCGCG CGTTGTTCAC CGGCGTTGCC GCCCACGCGA TTTCACCGTT GCCGTCACTG 360

GTGTCGGCCG GCGCCGGACT GATGCTGGCA ACGCTGGCCC ATTCGGTCGG CTGGCCGATT 420

CCGGTGGGCG GCACCCAGGC GATAGCCGAC GCGCTGATCG CCGATCTACG CGCGCATGGT 480

GGTCGGCTCG CGGCCGGTGT CGAGATCACC GAACCGCAAA GAAGTGTGGT CGTCTTCGAC 540

ACCGCACCCA CCGCCCTGCT GCGGGTTTAC CGCGACAAGC TTCCACATCG GTATGCCAAA 600

GCATTGCGCC GCTATCGATT TCGCGCTGGC ATCGCCAAGG TGGACTTCGT GCTCAGCGAC 660

GAGATCCCGT GGTCGGATCC GCGGCTGCGG CGGGCTGCGA CCCTGCATCT CGGCGGCACC 720

CGTGACCAGA TGGCGCGCGC CGAGGCAGAC GTCGCGGCGG GACGCCACGC CGACTGGCCG 780

ATGGTGCTGG CCGCGTGTCC GCACGTCGCC GACCCCGGCC GCATCGACGA AACCGGCCGC 840

CGTCCGTTCT GGACCTATGC CCACGTGCCG TCGGGGTCCA CGCTCGACGC GACCGAGACC 900

GTAACCAGCG TCCTCGAGCG GTTCGCCCCC GGCTTCCGTG ACATCGTGGT GGCGGGCCGC 960

GCCGTGCCCG CCGCGCGGAT GGCCGACCAC AACGCCAACT ACGTCGGCGG TGACATCACG 1020

GTCGGCGCCA ACTCGACCTG GCGCGCGATC GCCGGCCCCA CCCCGCGGTT GAATCCCTGG 1080

CGCACACCGA TTCCCAAGGT GTACCTGTGT TCTGCGGCGA CTCCGCCCGG CGCCGGCGTG 1140

CACGGCATGT GCGGCTGGTA TGCCGCTCGA ACGCTGTTGC GCACCGAGTT CGGCATCACC 1200

CGCATGCCCC CTTTGGGCCA TGAGCTGAGG CCATAACGAA GCTT 1244

(2) INFORMATION FOR SEQ ID NO:4:

(i) SEQUENCE CHARACTERISTICS:
(A) LENGTH: 414 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:4:

Glu Phe Asp Leu Pro Ala Arg Gly Val Thr Leu Thr Val Pro Asp Ile
1 5 10 15

Ala Tyr Ala Asn Pro Leu Pro Gly Arg Pro Ala Ala Ile Ala Tyr His
20 25 30

Asp Leu Ala His Thr Cys Ala Lys Leu Asp Asp Gly Ala Ser Trp Arg
35 40 45

-continued

```
Arg Leu Leu Gly Pro Leu Val Ala His Ser Glu Thr Val Val Glu Phe
    50                  55                  60

Met Leu Ser Asp Lys Arg Ser Leu Pro Thr Ala Leu Gly Ser Val Leu
65                  70                  75                  80

Arg Leu Gly Leu Arg Met Leu Ala Gln Gly Thr Pro Ala Trp Arg Ser
                85                  90                  95

Leu Ala Gly Glu Asp Ala Arg Ala Leu Phe Thr Gly Val Ala Ala His
            100                 105                 110

Ala Ile Ser Pro Leu Pro Ser Leu Val Ser Ala Gly Ala Gly Leu Met
        115                 120                 125

Leu Ala Thr Leu Ala His Ser Val Gly Trp Pro Ile Pro Val Gly Gly
    130                 135                 140

Thr Gln Ala Ile Ala Asp Ala Leu Ile Ala Asp Leu Arg Ala His Gly
145                 150                 155                 160

Gly Arg Leu Ala Ala Gly Val Glu Ile Thr Glu Pro Gln Arg Ser Val
                165                 170                 175

Val Val Phe Asp Thr Ala Pro Thr Ala Leu Leu Arg Val Tyr Arg Asp
            180                 185                 190

Lys Leu Pro His Arg Tyr Ala Lys Ala Leu Arg Arg Tyr Arg Phe Arg
        195                 200                 205

Ala Gly Ile Ala Lys Val Asp Phe Val Leu Ser Asp Glu Ile Pro Trp
    210                 215                 220

Ser Asp Pro Arg Leu Arg Arg Ala Ala Thr Leu His Leu Gly Gly Thr
225                 230                 235                 240

Arg Asp Gln Met Ala Arg Ala Glu Ala Asp Val Ala Ala Gly Arg His
                245                 250                 255

Ala Asp Trp Pro Met Val Leu Ala Ala Cys Pro His Val Ala Asp Pro
            260                 265                 270

Gly Arg Ile Asp Glu Thr Gly Arg Arg Pro Phe Trp Thr Tyr Ala His
        275                 280                 285

Val Pro Ser Gly Ser Thr Leu Asp Ala Thr Glu Thr Val Thr Ser Val
    290                 295                 300

Leu Glu Arg Phe Ala Pro Gly Phe Arg Asp Ile Val Val Ala Gly Arg
305                 310                 315                 320

Ala Val Pro Ala Ala Arg Met Ala Asp His Asn Ala Asn Tyr Val Gly
                325                 330                 335

Gly Asp Ile Thr Val Gly Ala Asn Ser Thr Trp Arg Ala Ile Ala Gly
            340                 345                 350

Pro Thr Pro Arg Leu Asn Pro Trp Arg Thr Pro Ile Pro Lys Val Tyr
        355                 360                 365

Leu Cys Ser Ala Ala Thr Pro Pro Gly Ala Gly Val His Gly Met Cys
    370                 375                 380

Gly Trp Tyr Ala Ala Arg Thr Leu Leu Arg Thr Glu Phe Gly Ile Thr
385                 390                 395                 400

Arg Met Pro Pro Leu Gly His Glu Leu Arg Pro Xaa Arg Ser
                405                 410
```

(2) INFORMATION FOR SEQ ID NO:5:

(i) SEQUENCE CHARACTERISTICS:
(A) LENGTH: 20 base pairs
(B) TYPE: nucleic acid
(C) STRANDEDNESS: single
(D) TOPOLOGY: linear -continued (ii) MOLECULE TYPE: cDNA (xi) SEQUENCE DESCRIPTION: SEQ ID NO:5:

CACCGAACCT CAAAGAAGTG 20

(2) INFORMATION FOR SEQ ID NO:6:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

GGATCCGACC AGGGATCTCG TCGC 24

(2) INFORMATION FOR SEQ ID NO:7:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

TACCCGCGCG CGGAGTGAC 19

(2) INFORMATION FOR SEQ ID NO:8:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

GACGCGCTGA TCGCCGATCT ACGCGCGCAT GGTGGTCGG 39

(2) INFORMATION FOR SEQ ID NO:9:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

CGGCAACGCC GGTGAACAAC GCGCGGGCAT CCTCGCCC 38

(2) INFORMATION FOR SEQ ID NO:10:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

-continued

```
CTACCCGCGC GCGGAGTGAC TCTGACC                                       27


(2) INFORMATION FOR SEQ ID NO:11:

     (i) SEQUENCE CHARACTERISTICS:
          (A) LENGTH: 38 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO:11:

CGGCAACGCC GGTGAACAAC GCGCGGGCAT CCTCGCCC                           38


(2) INFORMATION FOR SEQ ID NO:12:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO:12:

GGGGATGGCG GTGGGTGCGG TGTCG                                         25


(2) INFORMATION FOR SEQ ID NO:13:

     (i) SEQUENCE CHARACTERISTICS:
          (A) LENGTH: 39 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO:13:

GACGCGCTGA TCGCCGATCT ACGCGCGCAT GGTGGTCGG                          39
```

DNA MOLECULE CONFERRING ON *MYCOBACTERIUM TUBERCULOSIS* RESISTANCE AGAINST ANTIMICROBIAL REACTIVE OXYGEN AND NITROGEN INTERMEDIATES

This application claims priority to U.S. Provisional Patent Application Serial No. 60/045,688, filed May 6, 1997.

This invention arose out of research sponsored by the National Institutes of Health (Grant No. RO1-HL51967-01). The U.S. Government may have certain rights in this invention.

FIELD OF THE INVENTION

The present invention relates to a DNA molecule conferring on Mycobacterium tuberculosis resistance against antimicrobial reactive oxygen and nitrogen intermediates and its use in drugs, vaccines, and diagnostic tests.

BACKGROUND OF THE INVENTION

Tuberculosis is the leading cause of death in the world with an estimated 9 million new cases of tuberculosis and 2.9 million deaths occurring from the disease each year. In the United States, the steadily declining incidents of tuberculosis has been reversed since 1985. This problem is compounded by the increasing incidence of drug-resistant strains of Mycobacterium tuberculosis.

Recent outbreaks of tuberculosis have involved settings in which a large number of HIV-infected persons resided in close proximity (e.g., AIDS wards in hospitals, correctional facilities, and hospices). Transmission of tuberculosis to health care workers occurred in these outbreaks; 18 to 50% of such workers showed a conversion in their skin tests. See F. Laraque et. al., "Tuberculosis in HIV-Infected Patients," *The AIDS Reader* (September/October 1992), which is hereby incorporated by reference.

There are two basic clinical patterns that follow infection with Mycobacterium tuberculosis.

In the majority of cases, inhaled tubercle bacilli ingested by phagocytic alveolar macrophages are either directly killed or grow intracellularly to a limited extent in local lesions called tubercles. Infrequently in children and immunocompromised individuals, there is early hematogenous dissemination with the formation of small miliary (millet-like) lesions or life-threatening meningitis. More commonly, within 2 to 6 weeks after infection, cell-mediated immunity develops, and infiltration into the lesion of immune lymphocytes and activated macrophages results in the killing of most bacilli and the walling-off of this primary infection, often without symptoms being noted by the infected individual. Skin-test reactivity to a purified protein derivative ("PPD") of tuberculin and, in some cases, X-ray evidence of a healed, calcified lesion provide the only evidence of the infection. Nevertheless, to an unknown extend, dormant but viable Mycobacterium tuberculosis bacilli persist.

The second pattern is the progression or breakdown of infection to active disease. Individuals infected with Mycobacterium tuberculosis have a 10% lifetime risk of developing the disease. In either case, the bacilli spread from the site of initial infection in the lung through the lymphatics or blood to other parts of the body, the apex of the lung and the regional lymph node being favored sites. Extrapulmonary tuberculosis of the pleura, lymphatics, bone, genito-urinary system, meninges, peritoneum, or skin occurs in about 15% of tuberculosis patients. Although many bacilli are killed, a large proportion of infiltrating phagocytes and lung parenchymal cells die as well, producing characteristic solid caseous (cheese-like) necrosis in which bacilli may survive but not flourish. If a protective immune response dominates, the lesion may be arrested, albeit with some residual damage to the lung or other tissue. If the necrotic reaction expands, breaking into a bronchus, a cavity is produced in the lung, allowing large numbers of bacilli to spread with coughing to the outside. In the worst case, the solid necrosis, perhaps a result of released hydrolases from inflammatory cells, may liquefy, which creates a rich medium for the proliferation of bacilli, perhaps reaching $10^9$ per milliliter. The pathologic and inflammatory processes produce the characteristic weakness, fever, chest pain, cough, and, when a blood vessel is eroded, bloody sputum.

Two of the major antimicrobial mechanisms of activated macrophages depend on the synthesis of inorganic radical gases by immunologically regulated flavocytochrome complexes that use NADPH to reduce molecular oxygen. When oxygen is the sole co-substrate, the product is superoxide ($O_2$—)(Nathan, et al., "Mechanisms of Macrophage Antimicrobial Activity," *Trans. R. Soc. Trop. Med. Hyg.,* 77:620–30 (1983)); when L-arginine is an additional co-substrate, the product is nitric oxide (NO)(Nathan, et al., "Role of Nitric Oxide Synthesis in Macrophage Antimicrobial Activity," *Curr. Opin. Immunol.,* 3:65–70 (1991)). These radicals react with oxygen, transition metals, halides, sulfhydryls, and each other to produce a series of broadly cytotoxic products termed reactive oxygen intermediates ("ROI") and reactive nitrogen intermediates ("RNI"), as well as at least one compound with features of both, peroxynitrite (OONO—)(Butler, et al., "NO, Nitrosonium Ions, Nitroxide Ions, Nitrosothiols and Iron-Nitrosyls in Biology: A Chemist's Perspective," *Trends Pharmacol. Sci.,* 16:18–22 (1995) and DeGroote, et al., "NO Inhibitions: Antimicrobial Properties of Nitric Oxide," *Clin. Infect. Dis.,* 21:S162–5 (1995)).

Mycobacterium tuberculosis resist ROI by a diversity of mechanisms. Phenolic glycolipids (Neill, et al., "The Effect of Phenolic Glycolipid-1 From Mycobacterium Leprae on the Antimicrobial Activity of Human Macrophages," *J. Exp. Med.,* 167:30–42 (1988)) and cylcopropanated mycolic acids (Sherman, et al., "Disparate Responses to Oxidative Stress in Saprophytic and Pathogenic Mycobacteria," *Proc. Natl. Acad. Sci. USA,* 92:6625–9 (1995)) protect the cell wall, while catalase, alkylhydroperoxide reductase (Sherman, et al., "Compensatory ahpC Gene Expression in Isoniazid-Resistant Mycobacterium Tuberculosis," *Science,* 272:1641–3 (1996)) and superoxide dismutase (Dumarey, et al., "Selective Mycobacterium Avium-Induced Production of Nitric Oxide by Human Monocyte-Derived Macrophages," *J. Leuk. Biol.,* 56:36–40 (1994) and Zhang, et al., "Alterations in the Superoxide Dismutase Gene of an Isoniazid-Resistant Strain of Mycobacterium Tuberculosis," *Infect. Immun.,* 60:2160–5 (1992)) guard the cytosol. Moreover, Mycobacterium tuberculosis may enter macrophages via complement receptors (Chan, et al., "Immune Mechanisms of Protection. In Tuberculosis: Pathogenesis, Protection and Control," *B. R. Bloom, ed.* (*Washington:ASM*), 389–415 (1994) and Schlesinger, et al., "Phagocytosis of Mycobacterium Tuberculosis is Mediated by Human Monocyte Complement Receptors and Complement Component C3," *Immunol.,* 144:2271–80 (1990)), a pathway that fails to stimulate generation of ROI in some populations of macrophages (Wright, et al., "Receptors for C3b and C3bi Promote Phagocytosis But Not the Release of Toxic Oxygen From Human Phagocytes," *J. Exp. Med.,* 158:2016–2023 (1983)). The ability of Mycobacterium tuberculosis to mount such a broad defense against ROI implies that other products of the activated macrophage may be more important for tuberculostasis. Indeed, activated murine macrophages selectively deficient in production of ROI were nonetheless mycobactericidal (Chan, et al., "Killing of Virulent Mycobacterium Tuberculosis by Reactive Nitrogen Intermediates Produced by Activated Murine Macrophages," *J. Exp. Med.,* 175:1111–1122 (1992)). Not all mechanisms of defense against reactive oxygen intermediates are known.

In contrast, abundant evidence establishes the importance of RNI in the control of mycobacteria, at least in the mouse. Mycobacterium tuberculosis proliferates exuberantly in mice rendered selectively deficient in nitric oxide synthase type 2 (NOS2; iNOS). The organism also grows rapidly in mice made deficient in components of the cell-mediated immune response that normally leads to the induction of NOS2, as well as in mice dosed with organochemicals (Chan, et al., "Effects of Protein Malnutrition on Tuberculosis in Mice," *Proc. Natl. Acad. Sci. USA,* 93:14857–14861 (1996)) or glucocorticoids that inhibit the action or expression of NOS2. NOS2 is present in macrophages collected from the lungs of patients with tuberculosis (Nicholson, et al., "Inducible Nitric Oxide Synthase in Pulmonary Alveolar Macrophages From Patients With Tuberculosis," *J. Exp. Med.,* 183:2293–302 (1996)), raising the possibility that the enzyme may play an antitubercular role in people as well as in mice.

Ignorance of the molecular basis of virulence and pathogenesis is great. It has been suggested that the establishment of molecular evidence regarding avirulent strains, the identification and cloning of putative virulence genes of the pathogen, and the demonstration that virulence can be conveyed to an avirulent strain by those genes is necessary. Although avirulent strains of Mycobacterium tuberculosis exist, the nature of the mutations is unknown.

There have been many prescribed treatment regimens for tuberculosis. The regimen recommended by the U.S. Public Health Service and the American Thoracic Society is a combination of isoniazid, rifampicin, and pyrazinamide for two months followed by administration of isoniazid and rifampicin for an additional four months. In persons with HIV infection, isoniazid and rifampicin treatment are continued for an additional seven months. This treatment, called the short-course chemotherapy, produces a cure rate of over 90% for patients who complete it. Treatment for multi-drug resistant tuberculosis requires addition of ethambutol and/or streptomycin in the initial regimen, or second line drugs, such as kanamycin, amikacin, capreomycin, ethionamide, cyclcoserin, PAS, and clofazimine. New drugs, such as ciprofloxacin and ofloxacin can also be used. For individuals infected with conventional Mycobacterium tuberculosis and showing PPD positive results, chemoprophylaxis with isoniazid has been about 90% effective in preventing the disease. Tuberculosis and these treatments are discussed in more detail in B. Bloom et al., "Tuberculosis: Commentary on a Reemergent Killer," *Science,* 257:1055–64 (1992); "Control of Tuberculosis in the United States," *American Thoracic Society,* 146:1623–33 (1992); *City Health Information,* vol. 11 (1992), which are hereby incorporated by reference.

There has been a recent resurgence of tuberculosis in the United States due to the emergence of Mycobacterium tuberculosis strains which are resistant to isoniazid. Contrary to previous hypothesis, the drug resistant character of most of these strains is not believed to be caused by a complete deletion in the katG gene which encodes for an enzyme having catalase-peroxidase activity. Stoeckle, et. al., "Catalase-Peroxidase Gene Sequences in Isoniazid-Sensitive and -Resistant Strains of Mycobacterium tuberculosis in New York City," *J. Infect. Dis.* 168: 1063 65 (1993); Ferrazoli, et. al., "Catalase Expression, katG and MIC of Isoniazid for Mycobacterium tuberculosis Isolates from Sao Paulo, Brazil," *J. Infect. Dis.* 171: 237–40 (1995). It has since been hypothesized that another genetic locus, inhA, is the target for isoniazid action. Banerjee, et al., "inhA, a Gene Encoding a Target for Isoniazid and Ethionamide in Mycobacterium tuberculosis," *Science* 263: 227–30 (1994), but see Mdluli, et al., "Biochemical and Genetic Data Suggest that InhA is not the Primary Target for Activated Isoniazid in Mycobacterium tuberculosis," *J. Infect. Dis.* 174: 1085–90 (1996).

Although the currently used treatments for tuberculosis have a relatively high level of success, the need remains to improve the success rate for treating this disease. Moreover, in view of the ever-increasing level of Mycobacterium tuberculosis strains which are resistant to conventional treatment regimens, new types of treatment must be developed. In high tuberculosis endemic areas, both in the United States and abroad, such resistant strains are becoming increasing present.

SUMMARY OF THE INVENTION

The present invention relates to isolated DNA molecules conferring on Mycobacterium tuberculosis resistance against reactive oxygen intermediates (e.g., hydrogen peroxide and hypochlorite (HOCl)) antimicrobial reactive nitrogen intermediates (e.g., nitric oxide (NO), nitrite ($NO_2^-$), nitrosamine ($NO^+$), 5-nitrosothiols (RSNO), nitrogen dioxide ($NO_2$), dinitrogen trioxide ($N_2O_3$), and dinitrogen tetraoxide ($N_2O_4$) as well as isolated proteins or polypeptides encoded by these isolated DNA molecules. The molecule can be inserted as heterologous DNA in an expression vector forming a recombinant DNA expression system for producing the proteins or polypeptides. Likewise, the heterologous DNA, usually inserted in an expression vector to form a recombinant DNA expression system can be incorporated in a cell to achieve this objective.

The isolated protein or polypeptide of the present invention can be combined with a pharmaceutically-acceptable carrier to form a vaccine or used alone for administration to mammals, particularly humans, for preventing infection by Mycobacterium tuberculosis. Alternatively, the protein or polypeptide of the present invention can be used to raise an antibody or a binding portion thereof. The antibody or binding portion thereof may be used alone or combined with a pharmaceutically-acceptable carrier to treat mammals, particularly humans, already exposed to Mycobacterium tuberculosis to induce a passive immunity to prevent disease occurrence.

The proteins or polypeptides of the present invention or the antibodies or binding portions thereof raised against them can also be utilized in a method for detection of Mycobacterium tuberculosis in a sample of tissue or body fluids. When the protein or polypeptide is utilized, it is provided as an antigen. Any reaction with the antigen or the antibody is detected using an assay system which indicates the presence of Mycobacterium tuberculosis in the sample. Alternatively, Mycobacterium tuberculosis can be detected in such a sample by providing a nucleotide sequence of the gene conferring on Mycobacterium tuberculosis resistance against antimicrobial reactive oxygen and nitrogen intermediates as a probe in a nucleic acid hybridization assay or a gene amplication detecting procedure (e.g., using a polymerase chain reaction procedure). Any reaction with the probe is detected so that the presence of Mycobacterium tuberculosis in the sample is indicated.

The proteins or polypeptides of the present invention can be used to target therapeutic drugs. The proteins or polypeptides of the present invention can also be used for purposes unrelated to the treatment or detection of Mycobacterium tuberculosis.

Isolation of the DNA molecules of the present invention constitutes a significant advance in the treatment and detection of such bacteria. It also provides the basis for a vaccine to prevent infection by Mycobacterium tuberculosis and a pharmaceutical agent for passive immunization for those exposed to Mycobacterium tuberculosis. The proteins utilized in the vaccine or to produce the pharmaceutical agent can be produced at high levels using recombinant DNA technology.

In diagnostic applications, the proteins or polypeptides of the present invention as well as antibodies and binding portions thereof against them permit rapid determination of whether a particular individual is infected with Mycobacterium tuberculosis. Moreover, such detection can be carried out without requiring an examination of the individual being tested for an antibody response.

BRIEF DESCRIPTION OF THE DRAWINGS

FIG. 1A shows the survival of *E. coli* HB101 pBS (open squares) and HB101 pNO14 (solid squares) in ASN medium. Overnight cultures were diluted 100 fold in LB pH 5.3 containing 10 mM $NaNO_2$ and incubated at 37° C. Colony forming units (CFU) were determined at indicated times by plating serial dilutions on LB agar containing ampicillin. In this and subsequent panels, results are means±SE for triplicates; some error bars fall within the symbols. FIG. 1B shows the growth of Mycobacterium smegmatis pOLYG (open symbols) and Mycobacterium smegmatis pOLYG-NO14 (solid symbols) in 7H9 medium containing 30 mM sodium nitrite at pH 7.4 (triangles) or 30 mM sodium nitrate at pH 5.3 (squares). CFU were determined by plating on LB agar containing 50 μg/ml hygromycin, either at onset of culture or after 12 h. FIGS. 1C and 1D show the survival of M. smegmatis pOLYG (open squares) and M. smegmatis pOLYG-NO14 (solid squares) in ASN medium. Bacteria were grown to an optical density of $A_{600}$=4.5 (stationary phase cultures, FIG. 1C) or to $A_{600}$=1.5 (logarithmic phase cultures, FIG. 1D) and diluted 100 fold in 7H9 medium, pH 5.3, containing 30 mM $NaNO_2$. At indicated times, CFU were determined by plating appropriate dilutions on LB agar containing 50 μg/ml hygromycin.

FIGS. 2A–D contain a molecular analysis of the cloned DNA. In FIG. 2A, the presence of NOXR1 in different species of mycobacteria is analyzed. Chromosomal DNA (1 μg) of each strain was digested to completion with EcoRI and analyzed by Southern blotting with a digoxigenin-labeled probe corresponding to the 0.68 kb fragment from pNO14. Lane: 1, Mr markers; 2, Mycobacterium tuberculosis CB3.3; 3, Mycobacterium tuberculosis, H37Ra; 4, H37Rv; 5, Mycobacterium bovis; 6, Mycobacterium africanum; 7, Mycobacterium microti; 8, Mycobacterium fortuitum; 9, Mycobacterium smegmatis; 10, Mycobacterium avium; 11, Mycobacterium intracellulare; 12, Mycobacterium kansassi. FIG. 2B shows a map of the inserts in pNO14 and pNO16. FIG. 2C depicts the nucleotide sequence of the NO14 fragment and the amino acid sequence of the putative protein encoded by ORF1 (NOXR1). FIG. 2D shows a hydrophilicity plot of putative protein (NOXR1) encoded by ORF1.

FIG. 3A is a Northern Blot. Total RNA (15 μg) from Mycobacterium smegmatis pOLYG (lanes 1, 3) and Mycobacterium smegmatis pOLYG-NO14 (lanes 2, 4) was probed with oligonucleotides specific for ORF1 (lanes 1, 2) or ORF2 (lanes 3, 4). FIG. 3B is an RT-PCR analysis. Total RAN from recombinant Mycobacterium smegmatis stains (0.2 μg) and wild type Mycobacterium tuberculosis (1.0 μg) was analyzed by reverse transcriptase (RT) PCR after amplification of cDNA with random hexamer primers. Primer sets I and II specific for NOXR1 coding region are depicted. FIG. 3C shows the ablation of phenotype by introduction of a stop codon in ORF1. *E. coli* HB101 were transformed with pBS (open squares), pNO14.1 (solid squares), or pNO14.1-mut1 (solid triangles), the latter mutated to introduce a stop at codon 12 in ORF-1 without affecting ORF-2, and subjected to ASN.

FIGS. 4A–B show a time course of survival for *E. coli* HB101 transformed with pBS (open squares) or pNO14 (solid squares) and cultured in LB at pH 5.0 with (A) 2 mM GSNO or (B) 0.5 mM $H_2O_2$, as determined by the dye reduction microplate assay. FIGS. 4C–F show concentration-response curves for GSNO (FIGS. 4C and 4E) and $H_2O_2$ (FIGS. 4D–4F) after 6 h incubation at pH 5 (FIGS. 4C and 4D) or pH 7 (FIGS. 4E and 4F). FIGS. 4G–4H show the resistance to the combination of GSNO and $H_2O_2$ (0.1 mM); III, GSNO (5 mM); IV, $H_2O_2$ (0.1 mM); III, GSNO (1 mM); IV, $H_2O_2$ (0.05 mM)+GSNO (1 mM). Data in (FIGS. 4C and 4E) are means ±SE triplicates; some error bars fall within the symbols. Data in FIGS. 4G–4H are means of duplicates.

DETAILED DESCRIPTION OF THE INVENTION

Figure 1A:
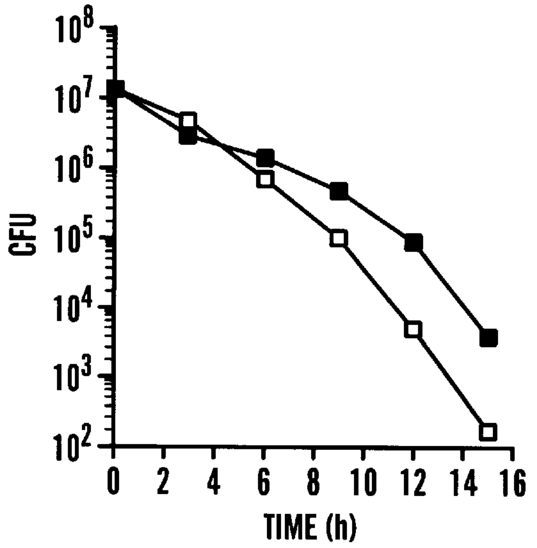
FIGS. 1A–D show how plasmid pNO14 from Mycobacterium tuberculosis confers enhanced survival on *E. coli* in acidified sodium nitrite.

One aspect of the present invention relates to an isolated DNA molecule conferring on Mycobacterium tuberculosis resistance against antimicrobial reactive oxygen and nitrogen intermediates. The term "isolated" is intended to define molecules which are separated from their naturally-present components (i.e., Mycobacterium tuberculosis). This DNA molecule comprises the nucleotide sequence corresponding to SEQ. ID. No. 1 as follows:

```
AAGCTTCGTT ATGGCCTCAG CTCATGGCCC AAAGGGGGCA TGCGGGTGAT GCCGAACTCG     60
GTGCGCAACA GCGTTCGAGC GGCATACCAG CCGCACATGC CGTGCACGCC GGCGCCGGGC    120
GGAGTCGCCG CAGAACACAG GTACACCTTG GGAATCGGTG TGCGCCAGGG ATTCAACCGC    180
GGGGTGGGGC CGGCGATCGC GCGCCAGGTC GAGTTGGCGC CGACCGTGAT GTCACCGCCG    240
ACGTAGTTGG CGTTGTGGTC GGCCATCCGC GCGGCGGGCA CGGCGCGGCC CGCCACCACG    300
ATGTCACGGA AGCCGGGGGC GAACCGCTCG AGGACGCTGG TTACGGTCTC GGTCGCGTCG    360
AGCGTGGACC CCGACGGCAC GTGGGCATAG GTCCAGAACG CACGGCGGCC GGTTTCGTCG    420
ATGCGGCCGG GGTCGGCGAC GTGCGGACAC GCGGCCAGCA CCATCGGCCA GTCGGCGTGG    480
CGTCCCGCCG CGACGTCTGC CTCGGCGCGC GCCATCTGGT CACGGGTGCC GCCGAGATGC    540
AGGGTCGCAG CCCGCCGCAG CCGCGGATCC GACCACGGGA TCTCGTCGCT GAGCACGAAG    600
TCCACCTTGG CGATGCCAGC GCGAAATCGA TAGCGGCGCA ATGCTTTGGC ATACCGATGT    660
GGAAGCTTGT CGCGGTAAAC CCGCAGCAGG GCGGTGGGTG CGGTGTCGAA GACGACCACA    720
CTTCTTTGCG GTTCGGTGAT CTCGACACCG GCCGCGAGCC GACCACCATG CGCGCGTAGA    780
TCGGCGATCA GCGCGTCGGC TATCGCCTGG GTGCCGCCCA CCGGAATCGG CCAGCCGACC    840
GAATGGGCCA GCGTTGCCAG CATCAGTCCG GCGCCGGCCG ACACCAGTGA CGGCAACGGT    900
GAAATCGCGT GGGCGGCAAC GCCGGTGAAC AACGCGCGGG CATCCTCGCC CGCCAGCGAC    960
CGCCAGGCAG GGGTGCCCTG GGCCAGCATC CGCAGCCCGA GACGCAGGAC CGAGCCCAGT   1020
GCAGTAGGCA AAGACCGCTT GTCGGAGAGC ATGAACTCCA CGACCGTCTC CGAGTGCGCC   1080
ACCAACGGGC CCAGCAGGCG CCGCCAGGAC GCGCCGTCGT CCAGCTTGGC GCAGGTGTGC   1140
GCCAGATCGT GATAGGCGAT CGCCGCGGGC CGCCCGGGTA GCGGGTTGGC GTAGGCGATG   1200
TCGGGCACGG TCAGCGTCAC TCCGCGCGCG GGTAGGTCGA ATTC                    1244
```

See also GenBank database accession no. Y08323 which is hereby incorporated by reference.

The above DNA molecule encodes for a cytoplasmic protein. The functional open reading frame is encoded by the nucleic acid spanning nucleotide 694 to nucleoties 1152 in SEQ. ID. No. 1. The deduced amino acid sequence corresponding to this open reading frame spanning nucleotide 694 to nucleotide 1152 of SEQ. ID. No. 1 is SEQ. ID. No. 2 as follows:

```
Val Gly Ala Val Ser Lys Thr Thr Thr Leu Leu Cys Gly Ser Val Ile
1               5                   10                  15

Ser Thr Pro Ala Ala Ser Arg Pro Pro Cys Ala Arg Arg Ser Ala Ile
            20                  25                  30

Ser Ala Ser Ala Ile Ala Trp Val Pro Pro Thr Gly Ile Gly Gln Pro
```

-continued

```
        35                  40                  45

Thr Glu Trp Ala Ser Val Ala Ser Ile Ser Pro Ala Pro Ala Asp Thr
    50                  55                  60

Ser Asp Gly Asn Gly Glu Ile Ala Trp Ala Ala Thr Pro Val Asn Asn
65                  70                  75                  80

Ala Arg Ala Ser Ser Pro Ala Ser Asp Arg Gln Ala Gly Val Pro Trp
                85                  90                  95

Ala Ser Ile Arg Ser Pro Arg Arg Arg Thr Glu Pro Ser Ala Val Gly
            100                 105                 110

Lys Asp Arg Leu Ser Glu Ser Met Asn Ser Thr Thr Val Ser Glu Cys
        115                 120                 125

Ala Thr Asn Gly Pro Ser Arg Arg Arg Gln Asp Ala Pro Ser Ser Ser
    130                 135                 140

Leu Ala Gln Val Cys Ala Arg Ser
145                 150
```

Production of this isolated protein or polypeptide is preferably carried out using recombinant DNA technology. The protein or polypeptide is believed to have one or more antigenic determinants conferring on Mycobacterium tuberculosis resistance against antimicrobial reactive oxygen and nitrogen intermediates.

The antisense version of the DNA molecule corresponding to SEQ. ID. No. 1 has an open reading frame corresponding to the nucleotide sequence of SEQ. ID. No. 3 as follows:

```
GAATTCGACC TACCCGCGCG CGGAGTGACG CTGACCGTGC CCGACATCGC CTACGCCAAC     60

CCGCTACCCG GGCGGCCCGC GGCGATCGCC TATCACGATC TGGCGCACAC CTGCGCCAAG    120

CTGGACGACG GCGCGTCCTG GCGGCGCCTG CTGGGCCCGT TGGTGGCGCA CTCGGAGACG    180

GTCGTGGAGT TCATGCTCTC CGACAAGCGG TCTTTGCCTA CTGCACTGGG CTCGGTCCTG    240

CGTCTCGGGC TGCGGATGCT GGCCCAGGGC ACCCCTGCCT GGCGGTCGCT GGCGGGCGAG    300

GATGCCCGCG CGTTGTTCAC CGGCGTTGCC GCCCACGCGA TTTCACCGTT GCCGTCACTG    360

GTGTCGGCCG GCGCCGGACT GATGCTGGCA ACGCTGGCCC ATTCGGTCGG CTGGCCGATT    420

CCGGTGGGCG GCACCCAGGC GATAGCCGAC GCGCTGATCG CCGATCTACG CGCGCATGGT    480

GGTCGGCTCG CGGCCGGTGT CGAGATCACC GAACCGCAAA GAAGTGTGGT CGTCTTCGAC    540

ACCGCACCCA CCGCCCTGCT GCGGGTTTAC CGCGACAAGC TTCCACATCG GTATGCCAAA    600

GCATTGCGCC GCTATCGATT TCGCGCTGGC ATCGCCAAGG TGGACTTCGT GCTCAGCGAC    660

GAGATCCCGT GGTCGGATCC GCGGCTGCGG CGGGCTGCGA CCCTGCATCT CGGCGGCACC    720

CGTGACCAGA TGGCGCGCGC CGAGGCAGAC GTCGCGGCGG GACGCCACGC CGACTGGCCG    780

ATGGTGCTGG CCGCGTGTCC GCACGTCGCC GACCCCGGCC GCATCGACGA AACCGGCCGC    840

CGTCCGTTCT GGACCTATGC CCACGTGCCG TCGGGGTCCA CGCTCGACGC GACCGAGACC    900

GTAACCAGCG TCCTCGAGCG GTTCGCCCCC GGCTTCCGTG ACATCGTGGT GGCGGGCCGC    960

GCCGTGCCCG CCGCGCGGAT GGCCGACCAC AACGCCAACT ACGTCGGCGG TGACATCACG   1020

GTCGGCGCCA ACTCGACCTG GCGCGCGATC GCCGGCCCCA CCCCGCGGTT GAATCCCTGG   1080

CGCACACCGA TTCCCAAGGT GTACCTGTGT TCTGCGGCGA CTCCGCCCGG CGCCGGCGTG   1140

CACGGCATGT GCGGCTGGTA TGCCGCTCGA ACGCTGTTGC GCACCGAGTT CGGCATCACC   1200

CGCATGCCCC CTTTGGGCCA TGAGCTGAGG CCATAACGAA GCTT                     1244
```

The nucleotide sequence of SEQ. ID. No. 3 encodes the amino acid of SEQ. ID. No. 4 as follows:

```
Glu Phe Asp Leu Pro Ala Arg Gly Val Thr Leu Thr Val Pro Asp Ile
1               5                   10                  15

Ala Tyr Ala Asn Pro Leu Pro Gly Arg Pro Ala Ala Ile Ala Tyr His
            20                  25                  30

Asp Leu Ala His Thr Cys Ala Lys Leu Asp Asp Gly Ala Ser Trp Arg
        35                  40                  45

Arg Leu Leu Gly Pro Leu Val Ala His Ser Glu Thr Val Val Glu Phe
    50                  55                  60

Met Leu Ser Asp Lys Arg Ser Leu Pro Thr Ala Leu Gly Ser Val Leu
65                  70                  75                  80

Arg Leu Gly Leu Arg Met Leu Ala Gln Gly Thr Pro Ala Trp Arg Ser
                85                  90                  95

Leu Ala Gly Glu Asp Ala Arg Ala Leu Phe Thr Gly Val Ala Ala His
            100                 105                 110

Ala Ile Ser Pro Leu Pro Ser Leu Val Ser Ala Gly Ala Gly Leu Met
        115                 120                 125

Leu Ala Thr Leu Ala His Ser Val Gly Trp Pro Ile Pro Val Gly Gly
    130                 135                 140

Thr Gln Ala Ile Ala Asp Ala Leu Ile Ala Asp Leu Arg Ala His Gly
145                 150                 155                 160

Gly Arg Leu Ala Ala Gly Val Glu Ile Thr Glu Pro Gln Arg Ser Val
                165                 170                 175

Val Val Phe Asp Thr Ala Pro Thr Ala Leu Leu Arg Val Tyr Arg Asp
            180                 185                 190

Lys Leu Pro His Arg Tyr Ala Lys Ala Leu Arg Arg Tyr Arg Phe Arg
        195                 200                 205

Ala Gly Ile Ala Lys Val Asp Phe Val Leu Ser Asp Glu Ile Pro Trp
    210                 215                 220

Ser Asp Pro Arg Leu Arg Arg Ala Ala Thr Leu His Leu Gly Gly Thr
225                 230                 235                 240

Arg Asp Gln Met Ala Arg Ala Glu Ala Asp Val Ala Ala Gly Arg His
                245                 250                 255

Ala Asp Trp Pro Met Val Leu Ala Ala Cys Pro His Val Ala Asp Pro
            260                 265                 270

Gly Arg Ile Asp Glu Thr Gly Arg Arg Pro Phe Trp Thr Tyr Ala His
        275                 280                 285

Val Pro Ser Gly Ser Thr Leu Asp Ala Thr Glu Thr Val Thr Ser Val
    290                 295                 300

Leu Glu Arg Phe Ala Pro Gly Phe Arg Asp Ile Val Val Ala Gly Arg
305                 310                 315                 320

Ala Val Pro Ala Ala Arg Met Ala Asp His Asn Ala Asn Tyr Val Gly
                325                 330                 335

Gly Asp Ile Thr Val Gly Ala Asn Ser Thr Trp Arg Ala Ile Ala Gly
            340                 345                 350

Pro Thr Pro Arg Leu Asn Pro Trp Arg Thr Pro Ile Pro Lys Val Tyr
        355                 360                 365

Leu Cys Ser Ala Ala Thr Pro Pro Gly Ala Gly Val His Gly Met Cys
    370                 375                 380

Gly Trp Tyr Ala Ala Arg Thr Leu Leu Arg Thr Glu Phe Gly Ile Thr
385                 390                 395                 400

Arg Met Pro Pro Leu Gly His Glu Leu Arg Pro Xaa Arg Ser
                405                 410
```

Fragments of the above polypeptides or proteins are also encompassed by the method of the present invention.

Suitable fragments can be produced by several means. In the first, subclones of the gene encoding a known protein are produced by conventional molecular genetic manipulation by subcloning gene fragments. The subclones then are expressed in vitro or in vivo in bacterial cells to yield a smaller protein or peptide that can be tested for activity in conferring resistance to reactive oxygen and reactive nitrogen intermediates.

As an alternative, protein fragments can be produced by digestion of a full-length protein with proteolytic enzymes like chymotrypsin or Staphylococcus proteinase A, or trypsin. Different proteolytic enzymes are likely to cleave proteins at different sites based on the amino acid sequence of the protein. Some of the fragments that result from proteolysis may be active in conferring resistance to reactive oxygen and nitrogen intermediates.

In another approach, based on knowledge of the primary structure of the proteins, fragments of the protein encoding gene may be synthesized by using the PCR technique together with specific sets of primers chosen to represent particular portions of the protein. These then would be cloned into an appropriate vector for increase and expression of a truncated peptide or protein.

Chemical synthesis can also be used to make suitable fragments. Such a synthesis is carried out using known amino acid sequences for the proteins being produced. Alternatively, subjecting a full length protein to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure, and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Suitable DNA molecules are those that hybridize to a DNA molecule comprising a nucleotide sequence of 50 continuous bases of SEQ. ID. Nos. 1 or 3 under stringent conditions characterized by a hybridization buffer comprising 0.9M sodium citrate ("SSC") buffer at a temperature of 37° C. and remaining bound when subject to washing with the SSC buffer at 37° C. and remaining bound when subject to washing with the SSC buffer at 37° C.; and preferably in a hybridization buffer comprising 20% formamide in 0.9M saline/0.09M SSC buffer at a temperature of 42° C. and remaining bound when subject to washing at 42° C. with 0.2× SSC buffer at 42° C.

The proteins or polypeptides of the present invention are preferably produced in purified form (preferably at least about 80%, more preferably 90%, pure) by conventional techniques. The proteins or polypeptides of the present invention are preferably produced in purified form by conventional techniques, of which the following is one example. To isolate the proteins, the *E. coli* host cell carrying a recombinant plasmid is propagated, homogenized, and the homogenate is centrifuged to remove bacterial debris. The supernantant is then subjected to sequential ammonium sulfate precipitation. The fraction containing the proteins of the present invention are subjected to gel filtration in an appropriately sized dextran or polyacrylamide column to separate the proteins. If necessary, the protein fraction may be further purified by HPLC.

Any one of the DNA molecules conferring on Mycobacterium tuberculosis resistance to antimicrobial reactive oxygen and nitrogen intermediates can be incorporated in cells using conventional recombinant DNA technology. Generally, this involves inserting the selected DNA molecule into an expression system to which that DNA molecule is heterologous (i.e. not normally present). The heterologous DNA molecule is inserted into the expression system or vector in proper orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, Sv 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual,* Colds Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology,* 68:473 (1979), which is hereby incorporated by reference.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli,* its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Additionally, any SD-ATG combination produced by recombinant DNA or other techniques involving incorporation of synthetic nucleotides may be used.

Once the desired isolated DNA molecule conferring on Mycobacterium tuberculosis resistance to antimicrobial reactive oxygen and nitrogen intermediates has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

From the present invention's determination of nucleotide sequences conferring on Mycobacterium tuberculosis resistance to antimicrobial reactive oxygen and nitrogen intermediates, a wide array of therapeutic and/or prophylactic agents and diagnostic procedures for, respectively, treating and detecting Mycobacterium tuberculosis can be developed.

For example, an effective amount of the proteins or polypeptides of the present invention can be administered alone or in combination with a pharmaceutically-acceptable carrier to humans, as a vaccine, for preventing infection by Mycobacterium tuberculosis. Alternatively, it is possible to administer to individuals exposed to Mycobacterium tuberculosis an effective amount of an antibody or binding portion thereof against these proteins or polypeptides as a passive immunization. Such antibodies or binding portions thereof are administered alone or in combination with a pharmaceutically-acceptable carrier to effect short term treatment of individuals who may have been recently exposed to Mycobacterium tuberculosis.

An additional therapeutic aspect of the present invention involves the administration of the subject DNA molecules to subjects requiring immunization against Mycobacterium tuberculosis. This is known as naked DNA vaccination where such DNA is injected into the muscles of subjects and enters cells, causing expression of the encoded protein. Ulmer, et. al., "Heterologous Protection Against Influenza by Injection of DNA Encoding a Viral Protein," *Science* 259: 1745–49 (1993), which is hereby incorporated by reference. The expressed protein has the same effect as if it were itself injected into the patient.

Antibodies suitable for use in inducing passive immunity can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest (i.e. one of the proteins or peptides of the present invention) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with one of the proteins or polypeptides of the present invention. Such immunizations are repeated as necessary at intervals of up to several weeks to obtain a sufficient titer of antibodies. The virus is carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents (See Milstein and Kohler, *Eur. J. Immuno.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering one of the proteins or polypeptides of the present invention subcutaneously to New Zealand white rabbits which have first been bled to obtain pre-immune serum. The antigens can be injected at a total volume of 100 $\mu$l per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed in E. Harlow, et. al., editors, *Antibodies: A Laboratory Manual* (1988), which is hereby incorporated by reference.

In addition to utilizing whole antibodies, the processes of the present invention encompass use of binding portions of such antibodies. Such antibody fragments can be made by conventional procedures, such as proteolytic fragmentation procedures, as described in J. Goding, *Monoclonal Antibodies: Principles and Practice,* pp. 98–118 (N.Y. Academic press 1983), which is hereby incorporated by reference.

The vaccines and passive immunization agents of this invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the proteins or peptides of the present invention or the antibodies or binding portions thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The DNA molecules of the present invention or the proteins or polypeptides of the present invention or the antibodies or binding portions thereof of this invention may also be administered in injectable dosages by solution or suspension of these materials in a physiologically acceptable diluent with a pharmaceutical carrier. Such carries include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the DNA molecules of the present invention or the proteins or polypeptides of the present invention or the antibodies or binding portions thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In yet another aspect of the present invention, the proteins or polypeptides of the present invention can be used as antigens in diagnostic assays for the detection of Mycobacterium tuberculosis in body fluids. Alternatively, the detection of that bacillus can be achieved with a diagnostic assay employing antibodies or binding portions thereof raised by such antigens. Such techniques permit detection of Mycobacterium tuberculosis in a sample of the following tissue or body fluids: blood, spinal fluid, sputum, pleural fluids, urine, bronchial alveolar lavage, lymph nodes, bone marrow, or other biopsied materials.

In one embodiment, the assay system has a sandwich or competitive format. Examples of suitable assays include an enzyme-linked immunosorbent assay, a radioimmunoassay, a gel diffusion precipitan reaction assay, an immunodiffusion assay, an agglutination assay, a fluorescent immunoassay, a protein A immunoassay, or an immunoelectrophoresis assay.

In an alternative diagnostic embodiment of the present invention, the nucleotide sequences of the isolated DNA molecules of the present invention may be used as a probe in nucleic acid hybridization assays for the detection of Mycobacterium tuberculosis in various patient body fluids. The nucleotide sequences of the present invention may be used in any nucleic acid hybridization assay system known in the art, including, but not limited to, Southern blots (Southern, *J. Mol. Biol.,* 98:508 (1975)); Northern blots (Thomas et al., *Proc. Nat'l Acad. Sci. USA,* 77:5201–05 (1980)); Colony blots (Grunstein et al., *Proc. Nat'l Acad. Sci. USA,* 72:3961–65 (1975)). All of these references are hereby incorporated by reference. Alternatively, the isolated DNA molecules of the present invention can be used in a gene amplication detection procedure (e.g., a polymerase chain reaction). See H. A. Erlich et. al., "Recent Advances in the Polymerase Chain Reaction", *Science* 252:1643–51 (1991), which is hereby incorporated by reference.

In addition to its use as a vaccine or in raising antibodies as an agent for passive immunization against Mycobacterium tuberculosis, the protein or polypeptide of the present invention has application as a therapeutic in treating conditions mediated by the production of reactive oxygen and reactive nitrogen intermediates. In this aspect of the present invention, advantage is taken of the ability of the subject protein or polypeptide to confer on Mycobacterium tuberculosis resistance against reactive oxygen and reactive nitrogen intermediates. Such compounds are part of the body's defense system against most infectious pathogens; however, by virtue of its ability to express the DNA molecule of the present invention, Mycobacterium tuberculosis is resistant to reactive oxygen and reactive nitrogen intermediates. It is also known, however, that reactive oxygen and reactive nitrogen intermediates have certain adverse effects on various physiological conditions, so the administration of the proteins or polypeptides of the present invention can be used to treat them. Here, the proteins or polypeptides of the present invention are administered to titrate the amounts of reactive oxygen and reactive nitrogen intermediates, thereby relieving a particular adverse condition. Administration of the proteins or polypeptides of the present invention can be carried out using the formulations and procedures discussed above.

Reactive nitrogen intermediates, particularly nitric oxide, are well known to mediate a number of adverse physiological conditions, including hypotension which accompanies sepsis. See Lowenstein, et. al., "Nitric Oxide: A Physiologic Messenger," *Ann. Intern. Med.* 120:227–37 (1994), which is hereby incorporated by reference. All of these conditions can be treated in accordance with the present invention.

The vasculature is in a constant state of active dilation mediated by nitric oxide. Endothelial cells continuously release small amounts of nitric oxide, producing a basal level of vascular smooth muscle relaxation. When nitric oxide is produced, vascular smooth muscle relaxes and blood pressure decreases. There are, however, adverse conditions mediated by overproduction of nitric oxides. For example, septic hypotension occurs when bacterial infection causes the massive release of nitric oxide which overwhelms the arterial smooth muscle and causes excess dilation and hypotension. When such a condition occurs, the proteins or polypeptides of the present invention can be administered to inhibit production of nitric oxide and, as a result, to increase blood pressure.

Excessive production of nitric oxides are also known to be triggered by strokes. Neurons release nitric oxide which diffuses into adjacent neurons in a series of steps. The presynaptic neuron is triggered by glutamate binding to the N-methyl-D-aspartate subtype receptor. This receptor possesses a calcium channel that opens, and the resulting influx of calcium binds to calmodulin to activate neuronal nitric oxide synthase. Nitric oxide is produced and diffuses out of the presynaptic neuron into the postsynaptic neuron, where it binds to the heme group of guanylate cyclase, activating the enzyme to produce cGMP. Small amounts of nitric oxide allow glutamate to increase cGMP levels in the brain. However, massive releases of glutamate during stroke trigger formation of large amounts of nitric oxide that are neurotoxic to adjacent neurons. Administration of the proteins or polypeptides of the present invention can be used to treat stroke victims.

As noted above, nitric oxides are produced by the body's immune system to kill various pathogens. However, the overproduction of nitric oxides for this purpose can have adverse effects. In some situations, the production of nitric oxides may damage normal cells in the body. It is not desirable to prevent production of nitric oxide, because this would permit growth of this infectious pathogen. However, some quenching of the nitric oxide product would be desirable. Thus, administration of the proteins or polypeptides of the present invention to titrate the produced nitric oxides would be desirable to quench overproduction of nitric oxides in response to infection by bacterial pathogens. This is different than the administration of agents which inhibit production of reactive nitrogen intermediates, because, here, there is no effort to control the enzymes producing nitric oxides (i.e. nitric oxide synthases), it is the material produced by the enzyme which is being controlled.

Lastly, the proteins or polypeptides of the present invention can be used to develop drugs for treating diseases caused by intracellular pathogen infection. This can be achieved by looking at the mechanism by which the proteins or polypeptides of the present invention resist reactive nitrogen intermediates. Such a mechanism may be conserved across other intracellular pathogens. If so, this knowledge can be used to design drugs that will target this resistance mechanism. Drugs to target such mechanisms may not have an in vitro activity. That is, such drugs may not inactivate or kill the organism outside of the cells. But, such drugs may allow the macrophages to kill efficiently the intracellular organism, if the organism's ability to resist the macrophage killing mechanism (i.e., reactive oxygen and reactive nitrogen intermediates) is inhibited by such drugs. Thus, these drugs can be designed to allow the normal macrophage antimicrobial molecules to exert their effects that may otherwise be resisted by the organism. This would be a new way to target bacterial killing. Alternatively, the DNA molecules of the present invention (or a portion thereof) can used as a probe to find other similar DNA molecules. The efficacy of such DNA molecules can be tested by producing recombinant bacteria, such as recombinant *E. coli*, which are transformed with this DNA molecule, and placing the recombinant and control bacteria in a medium containing nitric oxide or hydrogen peroxide and a therapeutic to be tested. Under these conditions, the control bacteria should always perish and the recombinant bacteria will perish only if the therapeutic has antibacterial effects.

EXAMPLES

Example 1

Bacterial Strains and Growth Conditions

*Mycobacterium smegmatis* mc 155 (Snapper, et al., "Isolation and Characterization of Efficient Plasmid Transformation Mutants of *Mycobacterium Smegmatis,*" *Mol. Microbiol*, 4:1911-9 (1990), which is hereby incorporated by reference, *M. tuberculosis* CB3.3 (Friedman, et al., "Transmission of Multidrug-Resistant Tuberculosis in a Large Urban Setting," *Am. J. Respir. Crit. Care Med.,* 152:355-9 (1995), which is hereby incorporated by reference) and other mycobacterial strains were grown in Middlebrook 7H9 broth (Difco) supplemented with 2% glycerol, 0.05% Tween 80, and ADC supplement (Difco) or plated on 7H11 agar (Difco). *Mycobacterium smegmatis* was plated on LB agar. LB broth or LB agar were used for *E. coli* strains XL1-Blue (Stratagene); HB101 (ATTC); DH5α (Gibco/BRL); M15 (Qiagen); GC4468 and DJ109 (Greenberg, et al., "Positive Control of a Global Antioxidant Defense Regulon Activated by Superoxide-Generating Agents in *Escherichia Coli,*" *Natl. Acad. Sci. USA,* 87:6181-5 (1990), which is hereby incorporated by reference), a SoxRS mutant, kindly provided by T. Nunoshiba and B. Demple, Harvard School of Public Health, Boston, Mass.; and JTG100 and its OxyR-deficient derivative, JTG101 (Greenberg, et al., "Overproduction of Peroxide-Scavenging Enzymes in *Escherichia Coli* Suppresses Spontaneous Mutagenesis and Sensitivity to Redox-Cycling Agents in OxyR-Mutants," *EMBO J.,* 7:2611-7 (1988), which is hereby incorporated by reference), also the kind gift of B. Demple. Ampicillin and hygromycin B (Sigma) were used at 100 μg/ml and 200 μg/ml, respectively, to grow *E. coli.* Hygromycin B was used at 50 μg/ml to grow mycobacteria.

Example 2

Plasmids pBluescript (Stratagene) served as a cloning vector and pQE31 (Qiagen) as an expression vector in *E. coli.* The shuttle vector pOLYG (a kind gift from Peadar O'Gaora and D. B. Young, Department of Medical Microbiology, St. Mary's Hospital Medical School, London, UK) is a derivative of p16R (Garbe, et al., "Transformation of Mycobacterial Species Using Hygromycin Resistance as Selectable Marker," *Microbiol,* 140:133-8 (1994), which is hereby incorporated by reference). pSMT3 is derived from pOLYG and contains the hsp60 promoter for overexpression of genes in mycobacteria (also a gift from P. O'Gaora).

Example 3

Cloning of *M. tuberculosis* DNA Fragment Associated with Resistance Against ROI and RNI Chromosomal DNA was isolated from *M. tuberculosis* CB3.3 as described (Van Soolingen, et al., "Occurrence and Stability of Insertion Sequences in *Mycobacterium Tuberculosis* Complex Strains: Evaluation of an Insertion Sequence-Dependent DNA Polymorphism as a Tool in the Epidemiology of Tuberculosis," *J. Clin. Microbiol.,* 29:2578-86 (1991), which is hereby incorporated by reference) and digested with EcoRI and BamHI. A genomic library was constructed by ligation of the DNA fragments into the *E. coli* vector pBluescript ("pBS"). *E. coli* XL-1-Blue was initially tested for growth in LB at various pH and $NaNO_2$ concentrations. At pH 6.0 and 6 mM $NaNO_2$, its growth was completely suppressed. Therefore, the genomic library was electroporated into strain XL1-Blue and the recombinants were screened for growth in LB at pH 6.0 containing 10 mM $NaNO_2$ (called ASN for acidified sodium nitride).

Example 4

Cloning of pNO16

To isolate a bigger plasmid containing the chromosomal fragment of pNO14, a library of *M. tuberculosis CB*3.3 genomic DNA was made by eluting partially Sau3A digested DNA (1.5–8 kb region) from an agarose gel and cloning it into the BamHI site of pBS. Transformants were subjected to colony hybridization (Sambrook, et al., *Molecular Cloning. A Laboratory Manual*, Second Edition: Cold Spring Harbor Laboratory Press), (1989), which is hereby incorporated by reference) using the 680 bp fragment of pNO14 as a probe. Two positive clones were identified and subjected to a second cycle of hybridization analysis. As a final product, plasmid pNO16 carrying a 4500 bp insert was isolated and its origin from *M. tuberculosis* CB3.3 as well as the integrity of the chromosomal DNA fragment was verified by Southern blot hybridization.

Example 5

Construction of pNO14.1 and its ORF-1 Mutant

A HindIII-SmaI fragment of pNO14 was cloned into the HindIII and HindII sites of pBS. The resulting plasmid, pNO14.1, still contains the complete ORF1. A point mutation was introduced at codon 12 of ORF1 (nucleotide 36 G→T), which created a stop codon (TGA) at that position. This mutation does not affect the amino acid sequence of the putative protein encoded by ORF2. The mutation was introduced by PCR mutagenesis using the following oligonucleotides; mut-1 (5'-caccgaacctcaaagaagtg-3') (SEQ. ID. No. 5) and no14-3 (5'-ggatccgaccagggatctcgtcgc-3') (SEQ. ID. No. 6) and pNO14 as a template. The 125 bp mutated fragment was isolated from an agarose gel and used as a primer in a second PCR. In this reaction, oligonugleotide no14-9 (5'-tacccgcgcgcggagtgac03') (SEQ. ID. No. 7) was used as the second primer. The amplified fragment containing the mutated ORF1 was digested with HindIII and SmaI and cloned into pBS, resulting in pNO14.1-mut1. The final construct was confirmed by sequencing.

Example 6

Analysis of the Resistant Phenotype

The relative resistance to chemically generated RNI was tested by inoculating a 1/100 dilution of the overnight or log-phase culture of the strain to be tested into 3 ml of LB pH 5.3 or 7H9 pH 5.3 containing $NaNO_2$ (Sigma) at various concentrations. Cultures were incubated at 37° C. for the indicated periods. The number of viable bacteria was determined by plating on LB agar. Alternatively, where indicated, a microplate assay was used that detects the ability of surviving bacteria to reduce a formulation of resazurin termed AlarmarBlue® (Sensitive Alamar, AccuMed International Companies, West Lake, Ohio) to a fluorescent product. Briefly, overnight cultures of bacteria were diluted 1:100 into LB titrated to the indicated pH and/or supplemented with $NaNO_2$, or to which the following compounds were added: GSNO (Alexis Biochemicals) or $H_2O_2$, NaCl or SDS (Sigma). At the indicated time points, 10 μl (out of 100 μl) was transferred to 100 μl LB containing 10% (v/v) AlamarBlue® (175 μM with respect to resazurin) in fresh 96-well plates. These plates were incubated at 37° C. while shaking at 75 rpm with a fluorescence reading taken every hour in a Cytofluor 2350 Fluorescence Measurement System (Millipore). The number of viable bacteria was deduced from a standard curve relating viable bacteria (by colony formation on agar plates) to the time required to reach a predetermined fluorescence.

Example 7

Northern Blot Analysis

RNA was isolated from 20 ml logarithmically growing mycobacterial cultures. Pelleted bacteria were resuspended in 1 ml TRIzol (Gibco/BRL). Zirconium/silica beads (0.5 mg; 0.1 mm; Biospec Products, Bartlesville, Okla.) were added and lysis performed in a FastPrep FP120 bead beater apparatus (BIO101) at 6000 rpm for 20 sec. The aqueous phase was extracted with chloroform and RNA precipitated with isopropanol. RNA was treated with RNase-free DNaseI for 1 h at 25° C., then incubated at 65° C. for 20 min and precipitated with ethanol. The pellet was resuspended in RNase-free water. The integrity of the RNA preparation was verified by the presence of two sharp rRNA bands, 1,500 and 3,100 nucleotides in length.

Two oligonucleotides, RNA-1 (5'-gacgcgctgatcgccgatctacgcgcgcatggtggtcgg-3') (SEQ. ID. No. 8) and RNA-2 (5'-cggcaacgccggtgaacaacgcgcgggcatcctcgccc-3') (SEQ. ID. No. 9) were labeled with dioxigenin using the oligonucleotide tailing kit (Boehringer Mannheim) to serve as probes for the transcripts of the two open reading frames, ORF1 and ORF2, respectively, RNA (15 μg) was separated by electrophoresis on a 1.5% agarose gel containing 0.66 M formaldehyde and transferred in 10×SSC (1.5 M NaCl, 0.15 M sodium citrate) to a positively charged nylon membrane (Boehringer Mannheim). The RNA was crosslinked to the membrane and prehybridized for 3–4 h at 42° C. in Dig-Easy-hybridization solution (Boehringer Mannheim). Hybridization was carried out in the presence of 100 pmol digoxigenin labeled oligonucleotide at 42° C. overnight. The membrane was washed twice for 5 min at RT with 2×SSC, 0.1% SDS and twice for 15 min at 68° C. with 0.1×SSC, 0.1% SDS. Detection of the hybridized digoxigenin labeled probe was performed using a chemiluminescent detection kit (Boehringer Mannheim).

Example 8

Reverse Transcriptase PCR

RT PCR was performed using Perkin Elmer Gene Amp RNA PCR Kit. Briefly, 0.2–1 μg total RNA was transcribed by Moloney MuLV reverse transciptase into cDNA with either random hexamer primers or a specific primer for the ORF1 RNA at 42° C. for 15 min. cDNA specific primers were added (Ia:5'-ctacccgcgcgcggagtgactctgacc-3'(SEQ. ID. No. 10); Ib: 5'-cggcaacgccggtgaacaacgcgcgggcatcctcgccc-3' (SEQ. ID. No. 11); IIa: 5'-ggggatggcggtgggtgcggtgtcg-3-' (SEQ. ID. No. 12); IIb: 5'-gacgcgctgatcgccgatctacgcgcgcatggtggtcgg-3-'(SEQ. ID. No. 13)) and the reaction was carried out with AmpliTaq DNA polymerase in a volume of 100 μl. The combined annealing and extending reaction was done at 60° C. for 30 sec.

Example 9

Protein Expression

NO14's ORF1 was cloned behind an inducible T5 promoter into the expression vector pQE-31 (Qiagen). This construct was electroporated into *E. coli* M15 (pREP4). M15 (pREP4) pQE-ORF1 were grown in LB containing 100 mg/l ampicillin and 25 mg/l kanamycin to an $OD_{580}$ of 1.0 and induced with 1.5 mM IPTG. After 4 h, bacteria were harvested and a sample of lysate was subjected to SDS-PAGE and Coomassie blue staining to check for overexpression of recombinant protein. Protein containing an N-terminal histidine tag was purified on Ni-NTA resin columns (Qiagen) and analyzed by SDS-PAGE. The N-terminal sequence of the purified protein was established for 19 residues, sufficient to read beyond the tag and 7 residues into NOXR1 proper. The purified protein was injected in female New Zealand White rabbits (4 injections of 100 mg NOXR1, at 4 wk intervals). The resulting antiserum was used for immunoblot analysis of bacterial lysates or purified protein by standard procedures. Affinity-purified antibody was prepared.

Example 10

Studies in Macrophages

An assay modified from that described (Buchmeier, et al., "Intracellular Survival of Wild-Type *Salmonella typhimurium* and Macrophage-Sensitive Mutants in Diverse Populations of Macrophages," *Infect. Immun.,* 57:1–7 (1989), which is hereby incorporated by reference) was used to determine the survival of *M. smegmatis* strains inside macrophages. Wild type ($iNOS^{+/+}$) and iNOS deficient mice ($iNOS^{-/-}$) (C57BL/6x129/SvEv) (MacMicking, et al. "Altered Responses to Bacterial Infection and Endotoxic Shock in Mice Lacking Inducible Nitric Oxide Synthase [Published Erratum Appears in Cell Jun. 30, 1995; 81(7): Following 1170]," *Cell,* 81:641–50 (1995), which is hereby incorporated by reference) and wild type and phox-91 deficient mice (C57BL6/J) (Pollock, et al., "Mouse Model of X-Linked Chronic Granulomatous Disease, an Inherited Defect in Phagocyte Superoxide Production," *Nat. Genet.,* 9:202–9 (1995), which is hereby incorporated by reference) were injected i.p. with 1.0 ml of sterile, freshly prepared 5 mM sodium periodate (Sigma) in phosphate buffered saline (PBS) 4 d before harvest. The mice were sacrificed by cervical dislocation or $CO_2$ inhalation. Peritoneal cells were harvested by lavage with 10 ml ice-cold sterile RPMI (Sigma), pH 7.2. Cells were collected by centrifugation for 10 min at 250xg at 4° C. and resuspended in PRMI medium supplemented with 10% heat inactivated fetal bovine serum (FBS) (HyClone, Logan, Utah), 1% glutamine (complete medium), and 10 μg/ml gentamicin. Viable cells were counted on a hemocytometer in the presence of trypan blue, and the proportion of macrophages determined by differential count of Diff-Quik stained Cytospin (Shandon, Sewickley, Pa.) preparations. Peritoneal cells ($4\times10^5$, ~50% macrophages) were plated in 96-well tissue-culture plates (Corning) at 100 μl per well. In some experiments, recombinant mouse IFN-γ (Genentech, South San Francisco, Calif.) was added at 50 U/ml. The plates were incubated at 30° C. in 5% $CO_2$, and, 12–24 h later, the adherent monolayers were washed twice with sterile PBS to remove gentamicin containing medium; complete removal required that the plates be emptied with a hard flick in each wash. Fresh complete medium±mIFN-γ was added, and 24–48 h after the initial plating, the cells were washed again with sterile PBS, and reconstituted with complete medium before infection.

Freshly electroporated *M. smegmatis* were grown to mid-log phase. Bacteria were opsonized in 10% fresh mouse serum for 30 min at 37° C., and 10 μl of the opsonized bacteria (~$2\times10^5$) were added to each well. The plates were centrifuged for 5 min at 250×g to synchronize the infection and then incubated at 37° C. for 30 min to allow phagocytosis. The wells were washed three times with sterile PBS to remove free bacteria. Complete medium (100 μl) containing 10 μg/ml gentamicin was added to each well, and the plates were incubated at 37° C. Gentamicin was added to prevent extracellular replication of mycobacteria that may not have been internalized or may have escaped from dying macrophages. Samples were taken at the indicated time points from individual wells in triplicate, as follows. The medium was removed and 50 μl aliquots were saved for nitrite determination. The cell monolayer was washed twice with PBS and lysed with 100 μl 0.1% sodium deoxycholate in PBS. Appropriate dilutions of the lysates were plated into LB plates containing 50 μg/ml hygromycin B for colony-forming unit (cfu) determinations.

To monitor macrophage production of NO, nitrite was measured in the culture supernatants as an accumulating oxidation product. The Griess reaction was performed as described by Ding, et al., "Release of Reactive Nitrogen Intermediates and Reactive Oxygen Intermediates From Mouse Peritoneal Macrophages: Comparison of Activating Cytokines and Evidence for Independent Production," *J. Immunol,* 141:2407–2412 (1988), which is hereby incorporated by reference. Conditioned medium (50 μl) was mixed with an equal amount of Griess reagent (1% sulphanilamide, 0.1% naphthylethylenediaminedihydrochloride, 2.5% $H_3PO_4$). After 10 min at RT, absorbance at 540 nm was measured and compared with standards using 1–100 μM of $NaNO_2^-$. The concentration of $NO_2^-$ in cell-free medium was subtracted to calculate the $NO_2^-$ contributed by macrophages. *M smegmatis* itself produced no detectable nitrite under the conditions of these experiments, as evidenced in cultures with $iNOS^{-/-}$ microphages (FIG. 7B inset).

Macrophage production of hydrogen peroxide was assessed by the horseradish peroxidase-catalyzed oxidation of fluorescent scopoletin to a nonfluorescent product, using a microplate format (De la Harpe, et al., "A Semi-Automated Micro-Assay for $H_2O_2$ Release by Human Blood Monocytes and Mouse Peritoneal Macrophages," *J. Immunol. Methods,* 78:323–36 (1985), which is hereby incorporated by reference).

Decreased production of $NO_2^-$ or hydrogen peroxide and diminished bactericidal activity could not be attributed to differential loss of macrophages from the monolayers, as monitored by measurements of adherent cell protein in the same cultures (De la Harpe, et al., "A Semi-Automated Micro-Assay for $H_2O_2$ Release by Human Blood Monocytes and Mouse Peritoneal Macrophages," *J. Immunol. Methods,* 78:323–36 (1985), which is hereby incorporated by reference).

Example 11

Cloning of an *M. tuberculosis* Gene Associated with Resistance to RNI

*E. coli* XL1-Blue was electroporated with a genomic library of *M. tuberculosis CB*3.3 and exposed for 24 h to acidified sodium nitrite (ASNA) (6 mM $NaNO_2$, pH 6.0). Protonation of $NaNO_2$ generates $HNO_2$, whose dismutation provides NO and nitrate, and, through reaction of NO with oxygen, other RNI (Stuehr, et al., "Nitric Oxide A Macrophage Product Responsible for Cytostasis and Respiratory Inhibition in Tumor Target Cells," *J. Exp. Med.,* 169:1543–1555 (1989) and Taylor, et al., "The Decomposition of Nitrous Acid in Aqueous Solutions," *J. Chem. Soc.,* 11:1923 (1927), which is hereby incorporated by reference). The main products of these reactions are probably dinitrogen tri- and tetra-oxides ($N_2O_3$ and $N_2O_4$) as well as S-nitrosothiols, which have profound bacteriostatic effects (Morris, et al., "Inhibition of Bacillus Cereus Spore Outgrowth by Covalent Modification of a Sulfhydryl Group By Nitrosothiol and Iodoacetate," *J. Bacteriol,* 148:465-41 (1981); Stamler, et al., "S-nitrosothiols and Bioregulatory Actions of Nitrogen Oxides Through Reactions With Thiol Groups," *Curr. Topics Microbiol. Immunol.* 196:19-36 (1995); and Stamler, et al., "Biochemistry of Nitric Oxide and Its Redox-Activated Forms," *Science,* 258:1898–1902 (1992), which are hereby incorporated by reference). ASN plays a physiologic role in the microbicidal system of the stomach (Dykhuizen, et al., "Antimicrobial Effect of Acidified Nitrite on Gut Pathogens: Importance of Dietary Nitrate in Host Defense," *Antimicrob. Agents Chemother,* 40:1422–1425 (1996), which is hereby incorporated by reference) and the combination of RNI and low pH also mimics aspects of the intraphagolysosomal milieu of the activated macrophage (Nathan, et al., "Role of Nitric Oxide Synthesis in Macrophage Antimicrobial Activity," *Curr. Opin. Immunol.* 3:35–70 (1991) and Sturgill-Koszycki, et al., "Lack of Acidification in Mycobacterium Phagosomes Produced by Exclusion of the Vesicular Proton-ATPase," *Science*, 263:678–681 (1994), which are hereby incorporated by reference). The chosen conditions killed *E. coli* XL1-Blue efficiently (>7 $\log_{10}$ in 24 h). Surviving transformants were detected with a frequency of $<10^{-6}$, and the recombinant plasmids were isolated. One such plasmid, called pNO14, consistently conferred upon XL1-Blue and four other *E. coli* hosts (DH5α, HB101, GC4468and JTG100) an enhanced ability to resist ASN. By 12 h, transformation of HB101 with pNO14 afforded a 50-fold increase in survival above transformation of the same *E. coli* host with the vector alone (FIG. 1A).

Figure 1B:
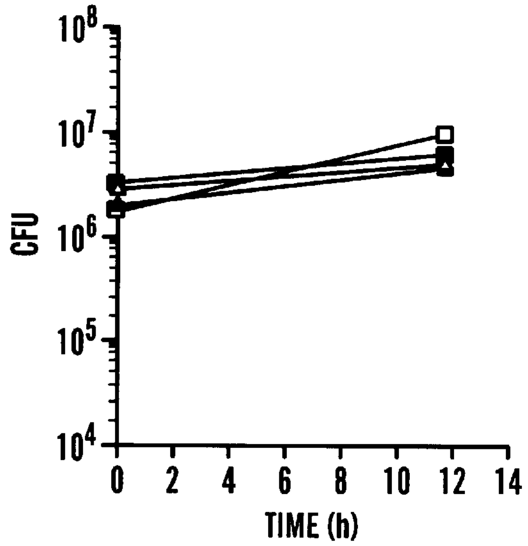

Means are not yet available for the facile genetic manipulation of *M. tuberculosis*. As a substitute mycobacterial species in which to analyze the function of pNO14, *M smegmatis* was chosen: the organism is fast-growing and easily transformable, and, as shown below, lacks a chromosomal copy of the gene carried by the pNO14. The 680 bp mycobacterial DNA fragment of pNO14 was cloned into the shuttle plasmid pOLYG (Garbe, et al., "Transformation of Mycobacterial Species Using Hygromycin Resistance as Selectable Marker," *Microbiol,* 140:133-8 (1994), which is hereby incorporated by reference) and electroporated into *M smegmatis* $mc^2$ 155 (Snapper, et al., "Isolation and Characterization of Efficient Plasmid Transformation Mutants of *Mycobacterium Smegmatis,*" *Mol. Microbiol,* 4:1911-9 (1990), which is hereby incorporated by reference). Neither the pOLYG-NO14—nor the vector-transformed strain was killed by sodium nitrate at pH 5.3, nor by sodium nitrite at pH 7.4 (FIG. 1B). These findings excluded a mycobactericidal effect of acid plus nitrate (the nonreactive dismutation product of $HNO_2$), and of nitrite under conditions that disfavor the formation of NO.

Figure 1C:
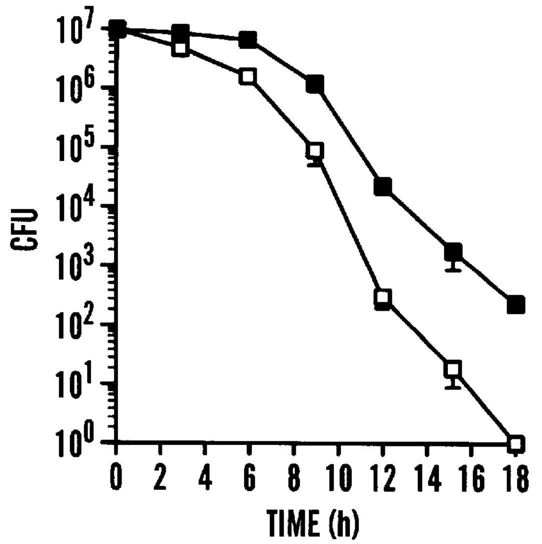
Figure 1D:
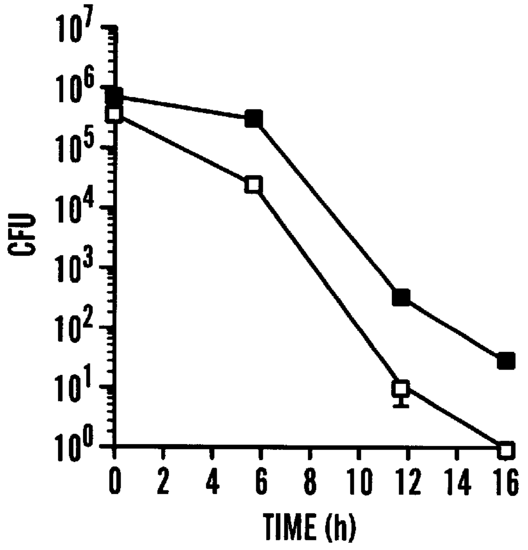

In contrast, when recombinant and control strains were exposed to nitrite at pH 5.3, both strains succumbed. Compared to its vector-transformed counterpart, *M. smegmatis* transformed with pOLYG-NO14 was increasingly less susceptible after 6 h, attaining a 100-fold relative advantage by 15 h (FIG. 1C). Logarithmically growing *M. smegmatis* (FIG. 1D) were more susceptible to ASN than those at stationary growth phase (FIG. 1C). However, the protective effect of pOLYG-NO14 was manifest in both phases. Thus, a gene product encoded by NO14 conferred relative resistance to RNI upon both *E. coli* and *M. smegmatis.*

Example 12

Expression Analysis

Figure 2A:
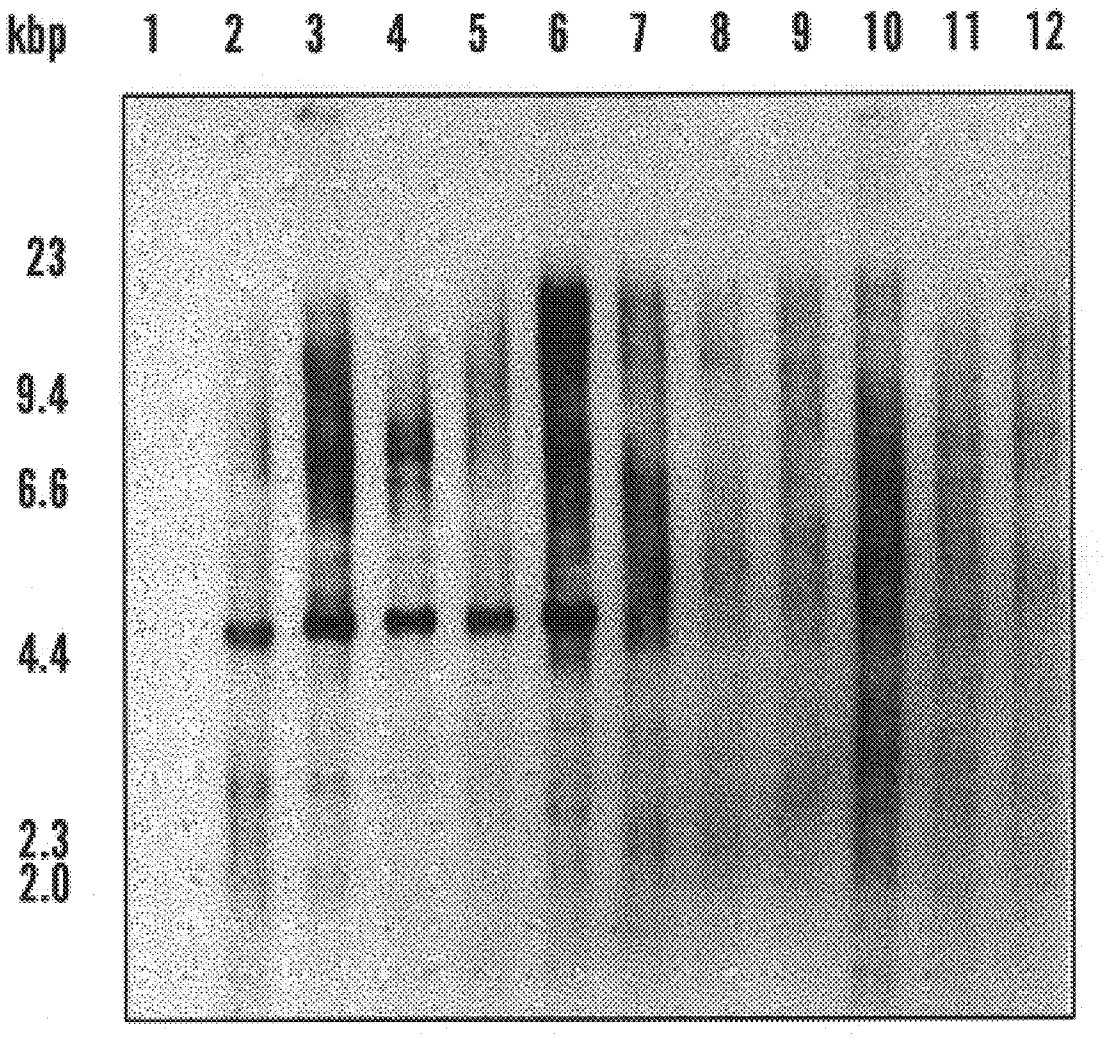

The cloned 680 bp fragment hybridized to genomes of all members of the *M. tuberculosis* complex except *M. microti*. None of the other mycobacterial strains tested hybridized with this probe (FIG. 2A). Thus, among mycobacteria, the cloned DNA appears to be specific for the members of the *M. tuberculosis* complex associated with human disease.

Plasmid pNO14's 680 bp EcoRI/BamHI fragment from *M. tuberculosis* included two overlapping open reading frames (ORFs) oriented in opposite directions (FIG. 2B). ORF1 encodes a putative protein of 152 amino acids (FIG. 2C) in an unusual pattern of alternating hydrophilic and hydrophobic segments that are shorter than typical membrane-spanning domains (FIG. 2D). The putative protein was predicted to have a Mr of 15,514 Da and a pI of 10.6, the basicity chiefly reflecting the relative abundance of Arg residues (9.2 mole percent). Despite the presence of four cysteines, no structural motifs were recognized, nor were there homologous sequences in the database. ORF2 did not contain a stop codon. A plasmid termed pNO16, which contained the full length ORF2, consisting of 1076 bases was isolated by colony hybridization (FIG. 2B). The putative protein encoded in ORF2 is 40% identical to XP55, a *Streptomyces lividans* secretory product of unknown function (Burnett, et al., "The Nucleotide Sequence of the Gene Coding for XP55, a Major Secreted Protein from *Streptomyces Lividans,*" *Nucl. Acids. Res.*, 19:3926 (1987), which is hereby incorporated by reference).

Figure 3A:
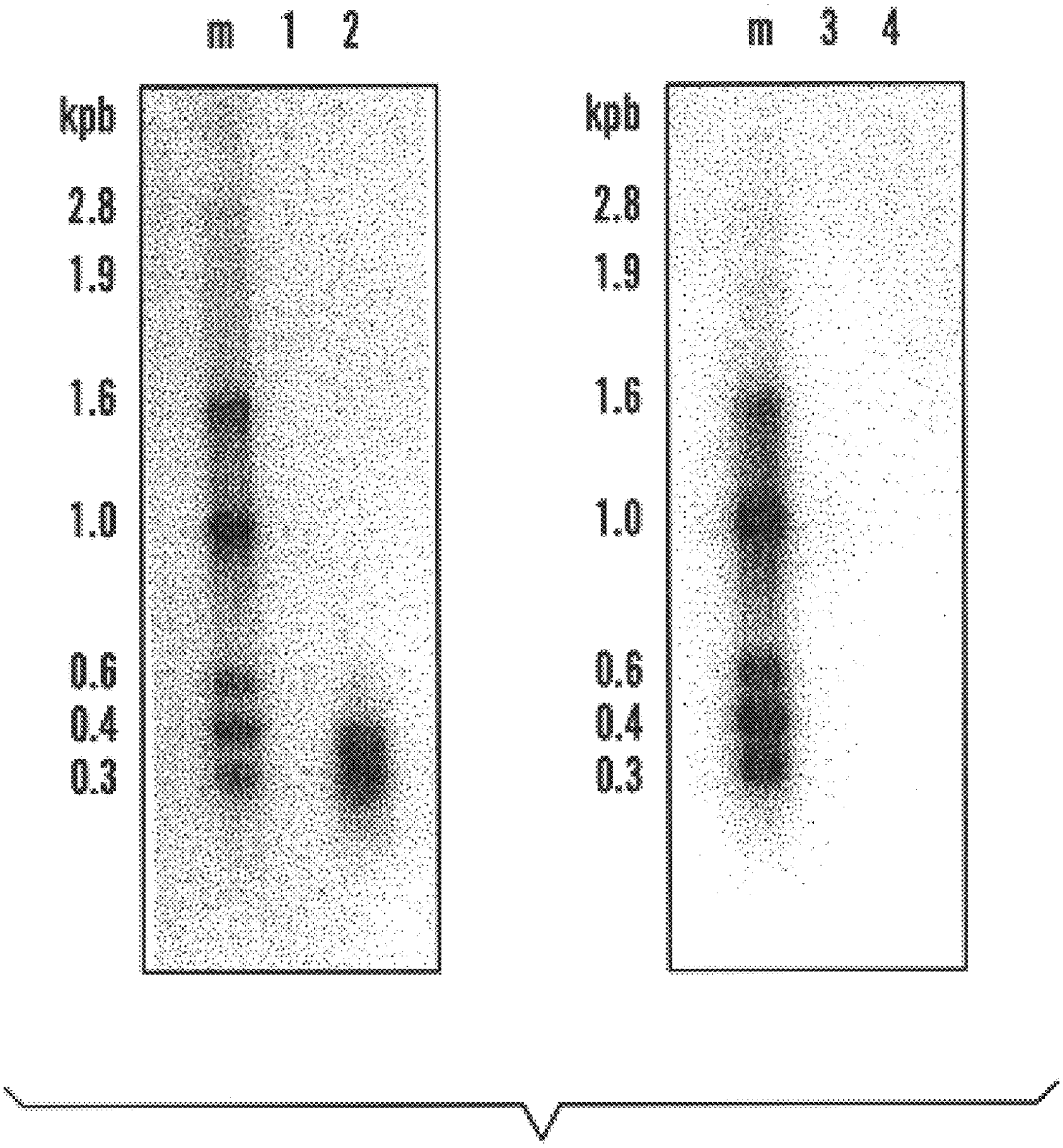
FIGS. 3A–C show the expression of recombinant NOXR1 in Mycobacterium smegmatis and native NOXR1 in Mycobacterium tuberculosis.

To find out which ORF was responsible for the observed phenotype, it was determined which was transcribed in recombinant *M. smegmatis.* In Northern blots with an oligonucleotide specific for ORF1, a ~400 bp transcript was detected in RNA purified from logarithmically growing *M. smegmatis* pOLYG-NO14 but not from *M. smegmatis* pOLYG (FIG. 3A). In contrast, neither RNA preparation hydribized with an oligonucleotide specific for ORF2. Exposure of *M. smegmatis* pOLYG-NO14 and *M. smegmatis* pOLYG to ASN before extraction of their RNA did not alter the Northern blot results, suggesting that ORF1 but not ORF2 was expressed during manifestation of the phenotype conferred by transformation with pOLYG-NO14. The gene corresponding to ORF1 was designated NOSR1.

Figure 3B:
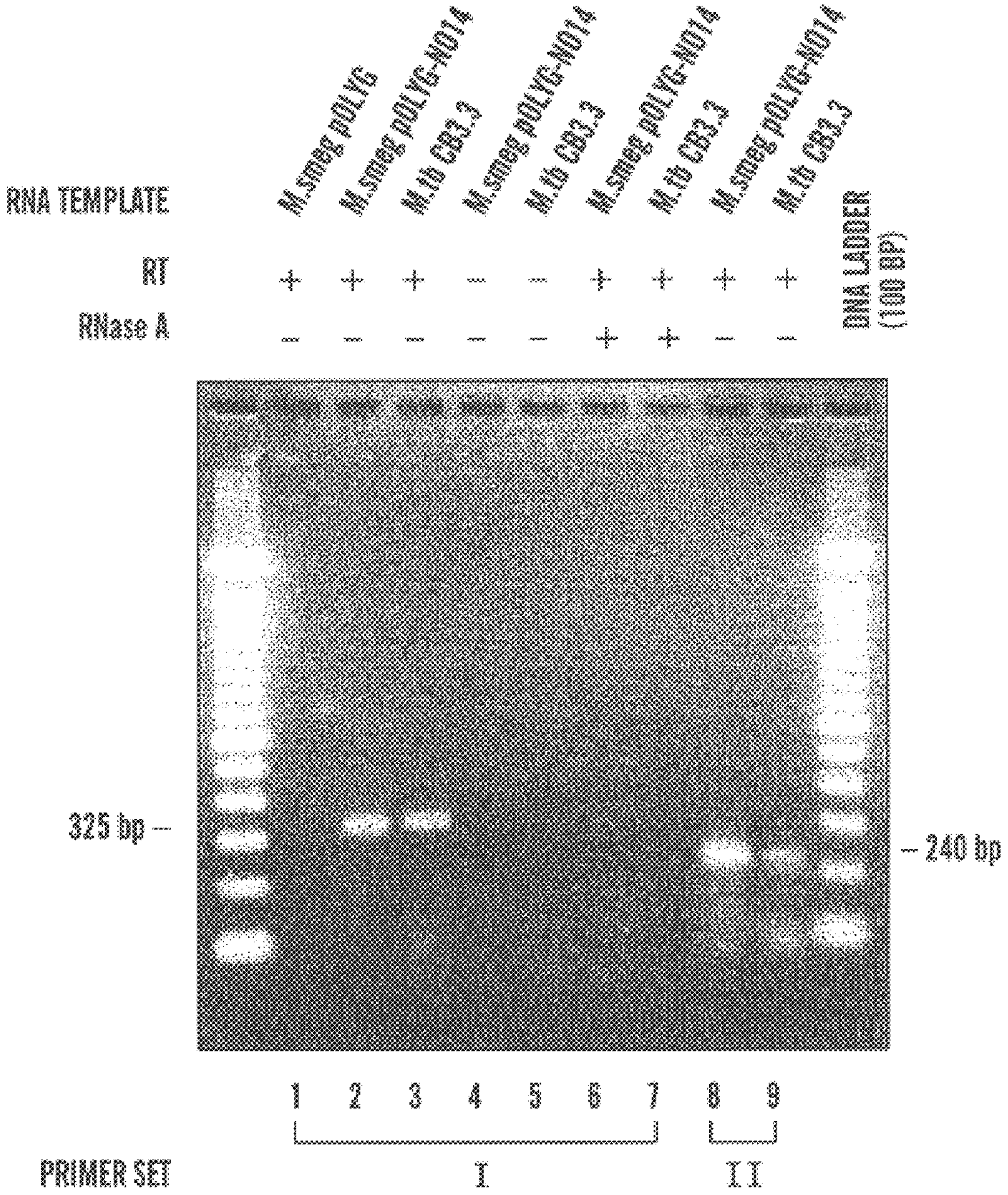
Figure 3B:
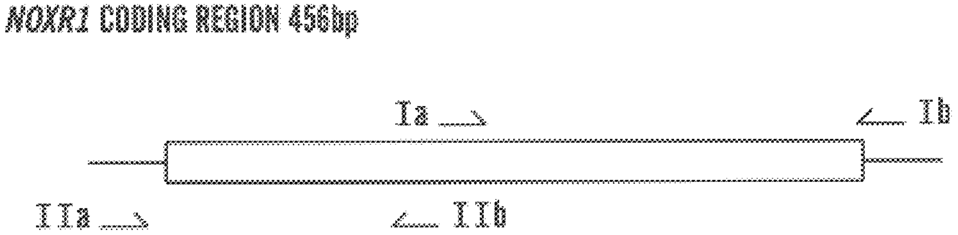

Northern blots were negative when the NOXR1 probe was applied to total RNA isolated from *M. tuberculosis* CB3.3. However, RT-PCR produced amplificands of the expected size (325 bp and 240 bp) with two different sets of primers specific for NOXR1 mRNA (FIG. 3B). No amplification occurred without reverse transcriptase or after adding RNAse A (FIG. 3B), excluding that the products were amplified from genomic sequences. Thus, NOXR1 was transcribed in *M. tuberculosis*.

Figure 3C:
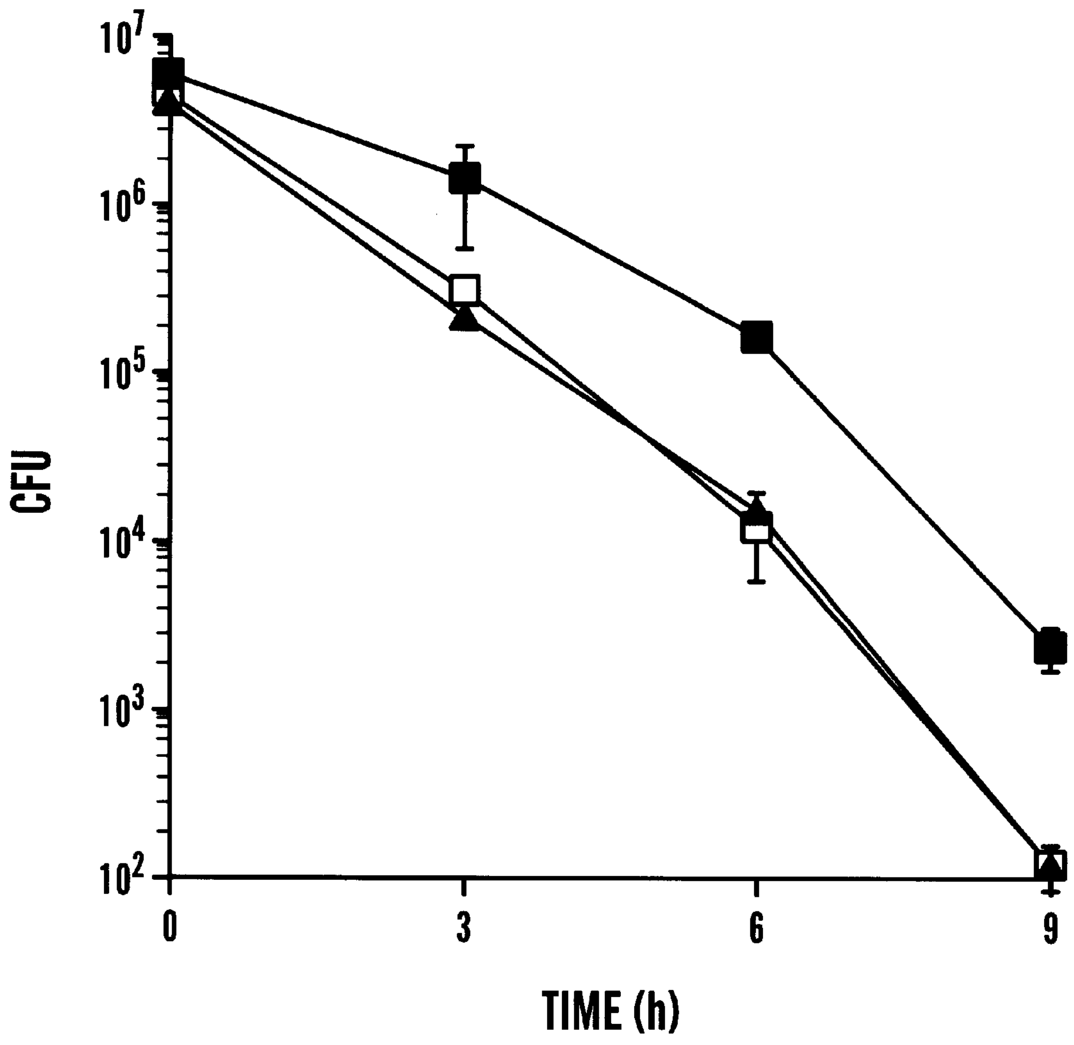

To analyze the expression of NOXR1 protein, affinity-purified antibody was prepared against a recombinant fusion protein. NOXR1 was cloned behind the inducible T5 promoter (pQE30-NOXR1) and overexpressed in *E. coli* M15 pREP4 in fusion with a hexahistidine-containing tag. Attempts to force high-level expression in *E. coli* M15 via pQE30-NOXR1 immediately led to inhibition of growth, and only a small amount of IPTG-induced product was recognizable by Coomassie blue staining of bacterial lysates separated by SDS-PAGE. A single polypeptide was, however, purified by nickel column chromatography with the expected Mr (17 kDa, based on the 15.5 kDa deduced Mr of NOXR1 plus 1.1 kDa for the fused tag). The purified protein was identified as NOXR1 by N-terminal amino acid sequencing, and no contaminating sequences were detected. The ostensibly pure NOXR1 was used to raise a rabbit antiserum. Antibody was affinity purified by subjecting chromatographically purified NOXR1 to SDS-PAGE and blotting NOXR1-containing gel slices to a nitrocellulose membrane, to which specific antibody was bound and eluted. The affinity-purified antibody did not detect any protein in *E. coli* HB101 dependent on transformation with pNO14. The techniques used for the immunoblot analysis may have been insufficiently sensitive to detect NOXR1 when it is expressed at low levels. Immunoblots were completely negative with *M. smegmatis* pOLYG-NO14 and *M. tuberculosis* CB3.3. Overexpression of NOXR1 in *M. smegmatis* using the hsp60 promoter was then attempted. As in *E. coli*, overexpression of the hsp60-NOXR1 translational fusion impaired the growth of *M. smegmatis*. Next, *E. coli* HB101 were transformed either with wild type NOXR1 or with a mutant in which a single base-pair change introduced a premature stop at codon 12 in ORF1, without affecting ORF2. Wild type NOXR1 encoded by pNO14.1, but no its ORF-1 mutant pNO14.1-mut1, protected the bacteria from ASN (FIG. 3C). Thus, it was possible to detect, purify, and sequence NOXR1 protein only when a NOXR1-fusion was overexpressed in association with toxicity; NOXR1 protein was not detected under conditions where lower levels of expression were presumed and a phenotype was conferred. Nonetheless, translation of the NOXR1 transcript appears to be required to confer resistance to ASN.

Example 13

NOXR1 also Confers Resistance to ROI and H+

Figure 4A:
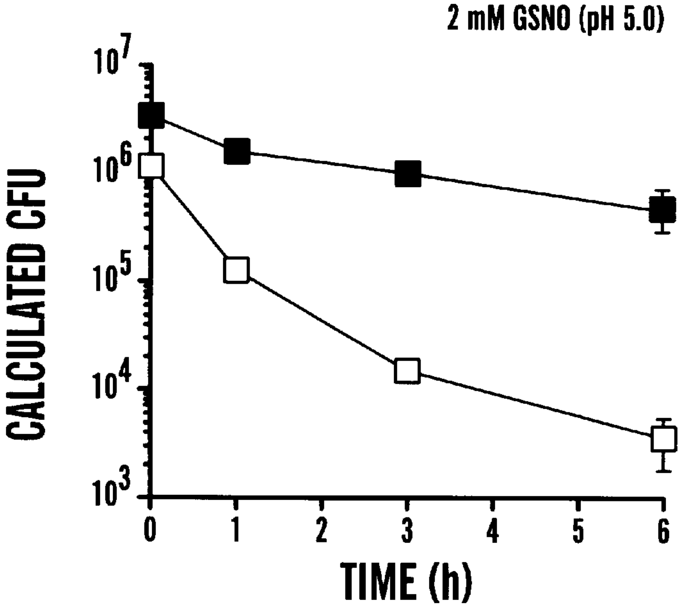
FIGS. 4A–H show the survival advantage conferred by NOXR1 on *E. coli* cultured in S-nitrosoglutathione and/or hydrogen peroxide.

To explore more fully the phenotype afforded by expression of NOXR1, a high-throughput, fluorescent, dye-reduction microplate assay whose results corresponded almost perfectly (correlation coefficients $r^2$>0.96) to the results of the more laborious colony-forming agar-plate assay after exposing bacteria to RNI in vitro or to the intraphagosomal milieu of macrophages was used. Not only was *E. coli* HB101 rendered far more resistant to ASN (2.5 mM $NaNO_2$, pH 5) by expression of NOXR1, but the bacteria also better resisted S-nitrosoglutathione (GSNO; 2 mM, pH 5.0), a physiologic and bacteriostatic (DeGroote, et al., "Genetic and Redox Determinants of Nitric Oxide Cytotoxicity in *Salmonella typhimurium* Model," *Proc. Natl. Acad. Sci. U.S.A,* 92:6399-403 (1995); DeGroote, et al., "Homocysteine Antagonism of Nitric Oxide-Related Cytostasis in *Salmonella typhimurium,*" *Science*, 272:414-7 (1996); and Morris, et al., "Inhibition of Bacillus Cereus Spore Outgrowth By Covalent Modification of a Sulfhydryl Group By Nitrosothiol and Iodoacetate," *J. Bacteriol,* 148:465-41 (1981), which are hereby incorporated by reference) source of several RNI, including ammonia (Lewis, et al., "Kinetic Analysis of the Fate of Nitric Oxide Synthesized by Macrophages in Vitro,"*J. Biol. Chem.,* 270:29350-5 (1995), which is hereby incorporated by reference) (FIGS. 4A, C). By 6 h, the survival advantage was close to 2 $log_{10}$. GSNO was more bactericidal at pH 5.0 (FIGS. 4A, C) than at pH 7.0 (FIG. 4E), but NOXR1 conferred protection under both conditions.

Figure 4B:
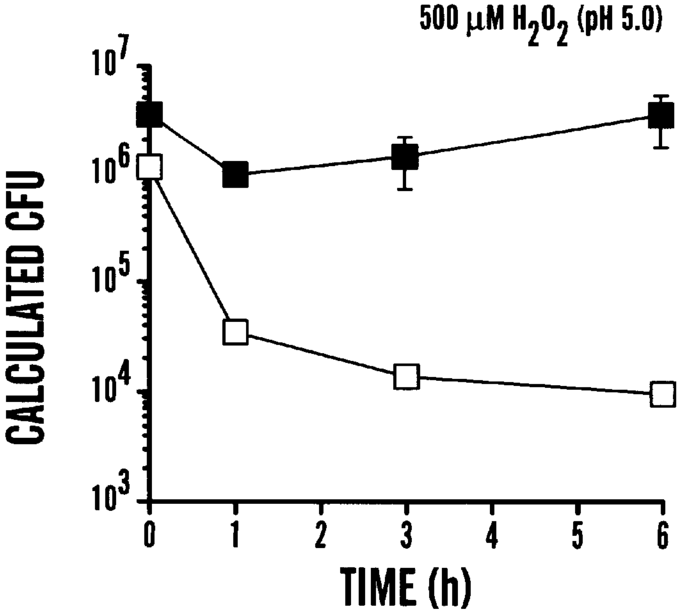
Figure 4C:
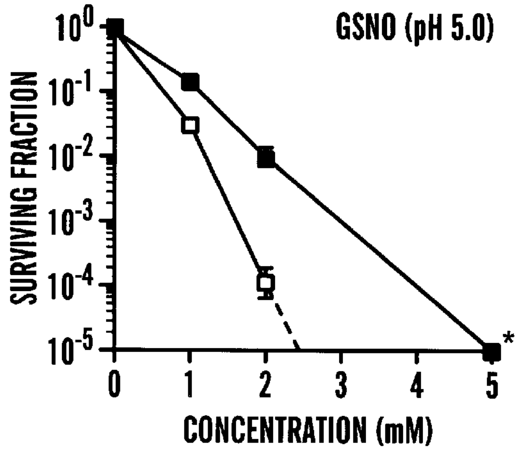
Figure 4D:
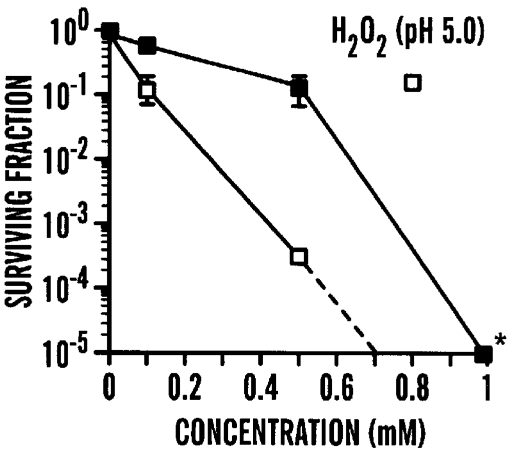
Figure 4E:
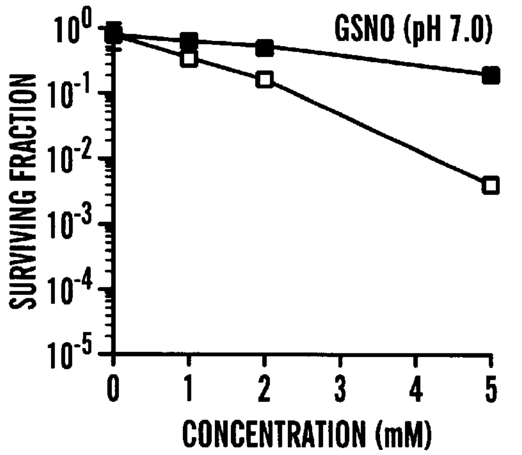
Figure 4F:
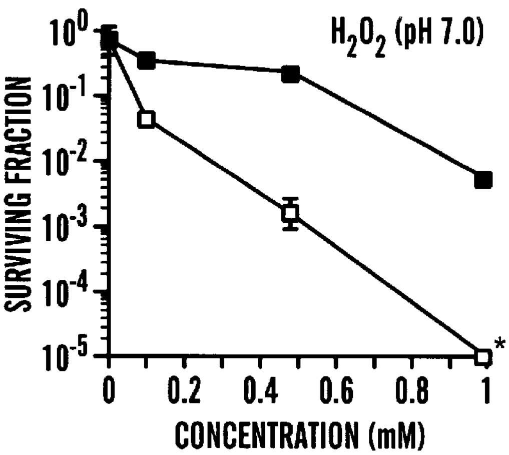
Figure 4G:
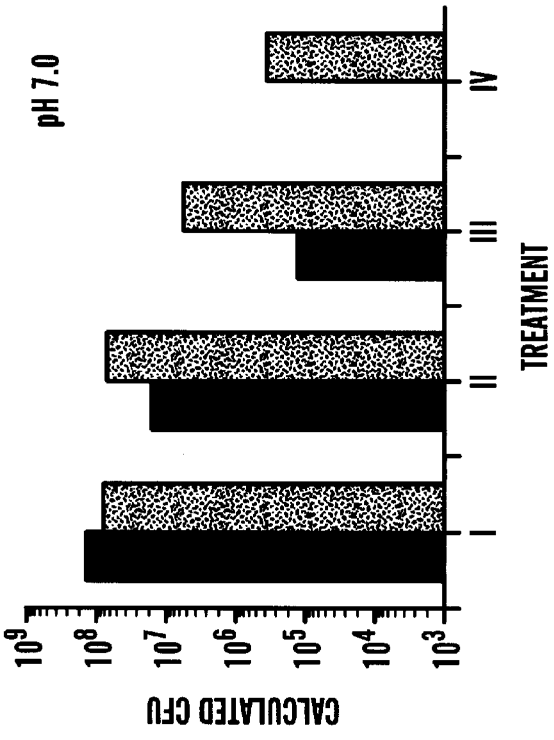
Figure 4H:
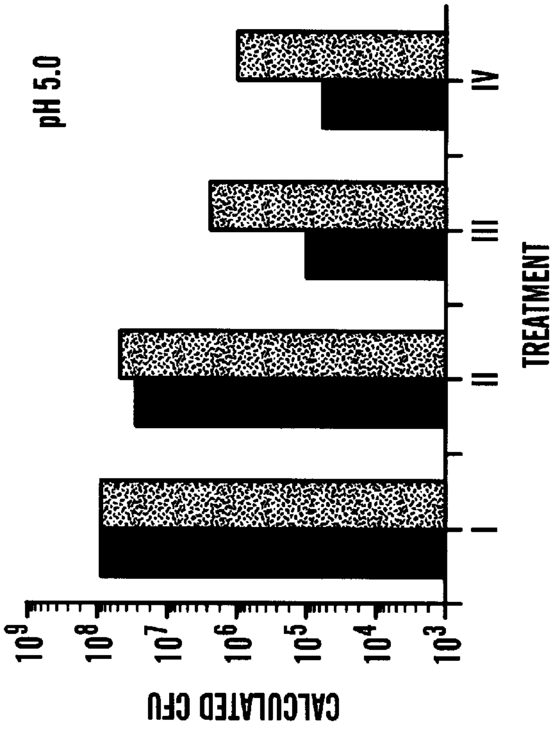

Unexpectedly, NOXR1 also conferred resistance to $H_2O_2$ (survival advantage, >2 $log_{10}$ by 6 h), and, in this case, pH had little bearing on the outcome (pH 5.0, FIGS. 4B, D; pH 7.0, FIG. 4F). Further, NOXR1 protected *E. coli* from the synergistic cytotoxicity afforded by GSNO plus $H_2O_2$ at concentrations of each agent that were harmless singly (FIG. 4G), or from the cytotoxicity afforded by the combination of three species likely to be present simultaneously in some phagosomes: GSNO, $H_2O_2$, and $H^+$ (FIG. 4H).

Figure 5A:
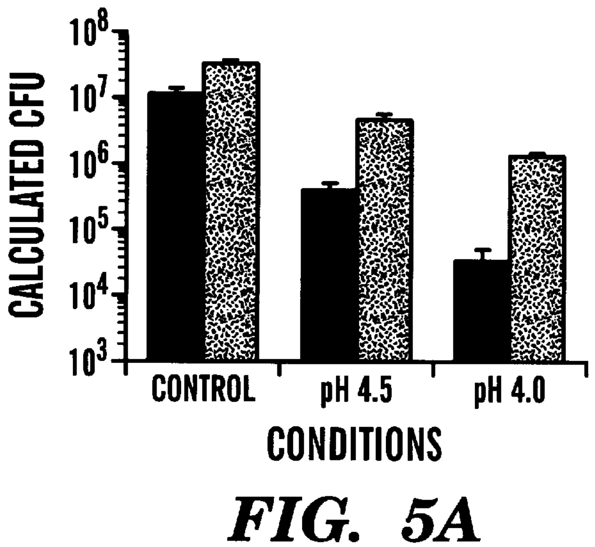
FIGS. 5A–C show the effect of transformation with NOXR1 on resistance of *E. coli* to low pH, osmotic stress or detergent. Survival of *E. coli* HB101 transformed with pBS (black bars) or pNO14 (gray bars) after 3 h incubation in LB medium with the following treatments: LB at pH 4.5 and pH 4.0 (FIG. 5A); addition of 0.5 M and 1.0 M NaCl (FIG. 5B); addition of 2% and 5% SDS (FIG. 5C). Control bars reflect growth at LB pH 7.0. Survival was quantified by a dye reduction microplate assay.
Figure 5B:
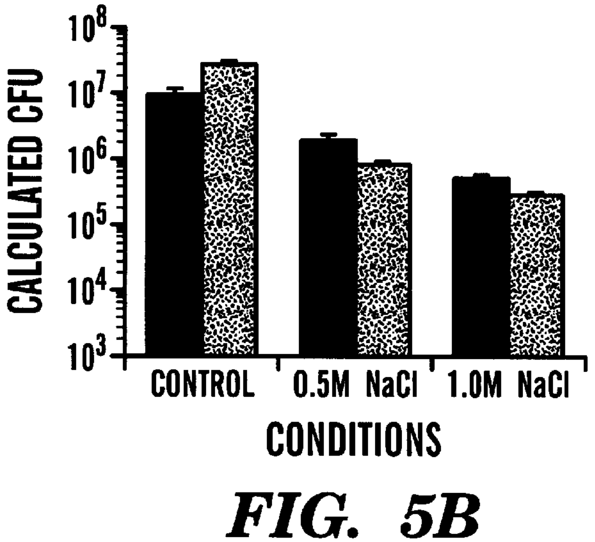
Figure 5C:
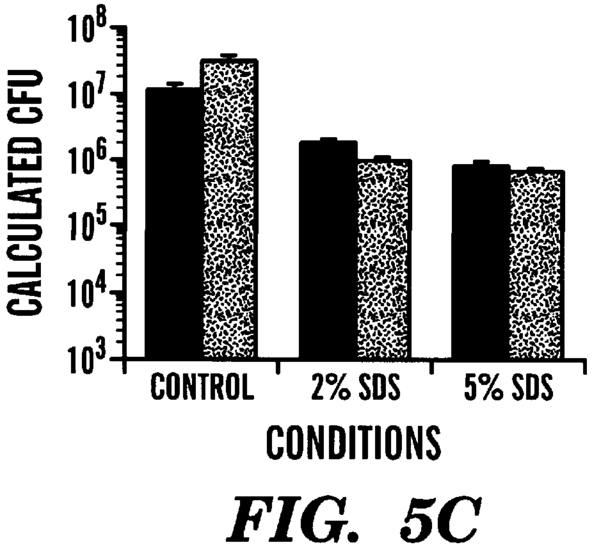
Figure 6A:
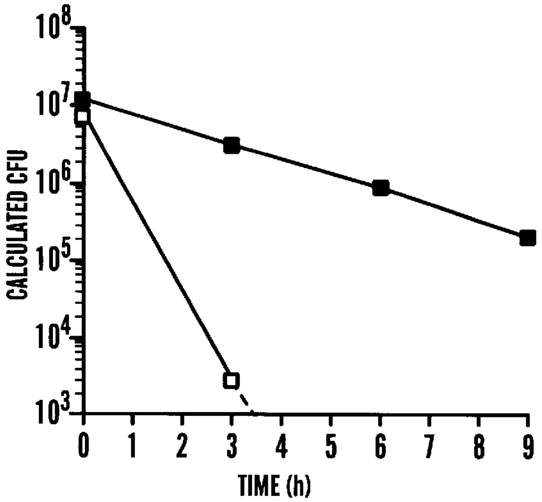
FIGS. 6A–D show that NOXR1-mediated resistance to acidified sodium nitrite is independent of OxyR and SoxRS. Survival of *E. coli* hosts transformed with pBS (open squares) and pNO14 (solid squares) in ASN medium are shown as follows: JTG100 (OxyR wt) (FIG. 6A); JTG101 (OxyR deficient) (FIG. 6B); GC4468 (SoxRs wt) (FIG. 6C); DJ901 (SoxRS deficient) (FIG. 6D). Overnight cultures were diluted 100 fold in LP pH 5.0 containing 10 mM $NaNO_2$ and incubated at 37° C. Resistance was quantified by a dye reduction microplate assay. Results are means±SE for triplicates; some error bars fall within the symbols.
Figure 6B:
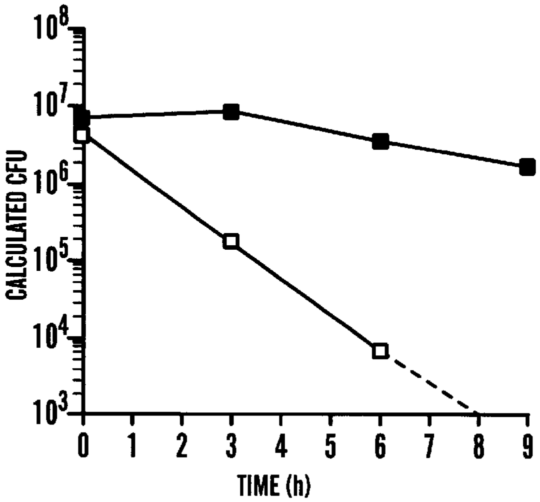
Figure 6C:
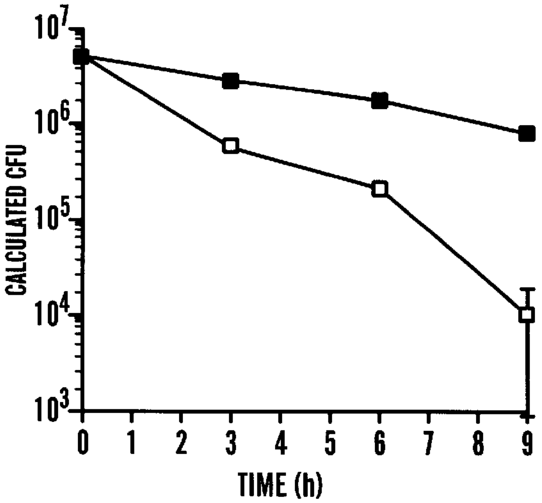
Figure 6D:
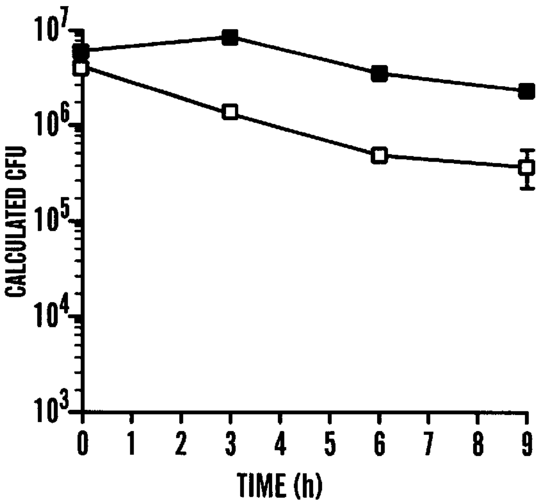

The results to this point did not allow distinguishing whether NOXR1 might protect relatively specifically against RNI and ROI, or might, instead, confer a general survival or repair function effective against virtually any threat to bacterial viability. The distinction can be hard to draw, since so many forms of insult, such as heat shock and ultraviolet irradiation, lead directly or indirectly to formation of ROI. Accordingly, NOXR1- and vector-transformed *E. coli* were subjected to three stresses in which generation of ROI has not apparently been implicated: elevated concentrations of $H^+$, sodium chloride, or detergent. NOXR1 did confer relative resistance to acid at pH 4.5, the lowest level reported in phagosomes (Ohkuma, et al., "Fluorescence Probe Measurement of the Intralysosomal pH in Living Cells and the Perturbation of pH by Various Agents," *Proc. Natl. Acad. Sci. USA,* 75:3327-31 (1978), which is hereby incorporated by reference) as well as to pH 4.0 (FIG. 5A). At pH's of 5 and above, no growth inhibition was detectable (FIG. 1B). In contrast, NOXR1 afforded no protection against the growth-inhibiting effects of high salt or SDS (FIGS. 5B, C).

Example 14

Independence of NOXR1 Effects from the OxyR and SoxRS Regulons

OxyR and SoxRS are multigenic regulons (Greenberg, et al., "Positive Control of a Global Antioxidant Defense Regulon Activated by Superoxide-Generating Agents in *Escherichia Coli,*" *Natl. Acad. Sci. USA,* 87:6181-5 (1990), which is hereby incorporated by reference), each of which is activated by and confers resistance to both ROI and RNI in *E. coli* (Hausladen, et al., "Nitrosative Stress-Activation of the Transcription Factor OxyR," *Cell,* 86:719–729 (1996); Nunoshiba, et al., "Roles of Nitric Oxide in Inducible Resistance of *Escherichia Coli* to Activated Macrophages," *Infect. Immun.,* 63:794–798 (1995); and Nonoshiba, et al., "Activation by Nitric Oxide of an Oxidative-Stress Response That Defends *Escherichia Coli* Against Activated Macrophages," *Proc. Natl. Acad. Sci. USA*, 90:993–9997 (1993), which are hereby incorporated by reference). In *M. tuberculosis*, OxyR is disrupted and SoxRS is undescribed (Dhandayuthapani, et al., "Oxidative Stress Response and Its Role in Sensitivity to Isoniazid in Mycobacteria: Characterization and Inducibility of ahpC by Peroxides in Mycobacterium Smegmatis and Lack of Expression in M. Aurum and M. Tuberculosis," *J. Bacteriol,* 178:3641-9 (1996); Sherman, et al., "Compensatory ahpC Gene Expression in Isoniazid-Resistant *Mycobacterium Tuberculosis,*" *Science,* 272:1641-3 (1996); Sherman, et al., "Disparate Responses to Oxidative Stress in Saprophytic and Pathogenic Mycobacteria," *Proc. Natl. Acad. Sci. USA,* 92:6625-9 (1995); and Zhang, et al., "Molecular Basis For the Exquisite Sensitivity of *Mycobacterium Tuberculosis* to Isoniazid," 93:13212–13216 (1996), which are hereby incorporated by reference), whereas in *E. coli*, neither regulon contains any sequence homologous to NOXR1. Nonetheless, it was desired to test whether NOXR1 from *M. tuberculosis* might function in recombinant *E. coli* through activation of OxyR or SoxRS. The genes controlled by these factors number at least 19, including those encoding superoxide dismutase, NADPH:ferredoxin oxidoreductase, fumarase, DNA repair endonuclease IV, catalase, alkylhydroperoxide reductase, and glutathione reductase. Accordingly, *E. coli* deficient in either of these two regulons and their corresponding wild type strains with pNO14 or PBS vector alone were transformed. In all four hosts, NOXR1 conferred resistance to ASN (FIG. 6). The degree of protection depended on the host cell type, but not on its expression of OxyR or SoxRS. Thus, genes dependent upon OxyR or SoxRS are dispensable for the function of NOXR1, unless NOXR1 can substitute for OxyR or SoxRS to induce their expression.

Example 15

Effect of NOXR1 on Survival of *M. smegmatis* Within Macrophages

The observations that NOXR1 protects *M. smegmatis* from the antibacterial effects of RNI and ROI in vitro prompted exploration of the effect of this gene on the survival of *M. smegmatis* inside activated macrophages, where the full complement of antibacterial mechanisms is undefined.

Macrophages were collected from the peritoneal cavity of mice 4 days following intraperitoneal injection of sodium periodate (Weinberg, et al., "In Vitro Modulation of Macrophage Tumoricidal Activity: Partial Characterization of a Macrophage-Activating Factor(s) in Supernatants of NaIO4-Treated Cells," *J. Retibuloendothel. Soc.,* 26:283–93 (1997), which is hereby incorporated by reference). Periodiate, a lymphocyte mitogen, stimulates cytokine production (Novogrodsky, et al., "Selective Activation of Mouse T and B Lymphocytes by Periodate, Galactose Oxidase and Soybean Agglutinin," *Eu. J. Immunol.,* 4:646-8 (1974), which is hereby incorporated by reference). Macrophages from periodate-injected mice have a respiratory burst capacity typical of macrophages activated by infection of the host with mycobacteria (Nathan, et al., "Hydrogen Peroxide Release From Mouse Peritoneal Macrophages: Dependence on Sequential Activation and Triggering," *J. Exp. Med.,* 146:1648-62 (1977), which is hereby incorporated by reference) or macrophages treated in vitro with cytokines (Nathan, et al., "Identification of Interferon-Gamma as the Lymphokine That Activates Human Macrophage Oxidative Metabolism and Antimicrobial Activity," *J. Exp. Med.,* 158:670-89 (1983), which is hereby incorporated by reference). Periodate-elicited macrophages respond to further inductive signals, such as in vitro incubation with interferonγ (IFN-γ), by producing NO (Ding, et al., "Release of Reactive Nitrogen Intermediates and Reactive Oxygen Intermediates From Mouse Peritoneal Macrophages: Comparison of Activating Cytokines and Evidence For Independent Production," *J. Immunol,* 141:2407–2412 (1988), which is hereby incorporated by reference). Both properties were confirmed in wild type macrophages in the present experiments; in addition, *M. smegmatis* alone was sufficient to trigger NO production in periodate-elicited macrophages without exposure to exogenous cytokines in vitro (FIG. 7 insets).

In order to vary the genotype of the macrophages along with that of the mycobacteria, wild type mice of C57BL/6x129/SvEv background were matched with NOS2-deficient mice on the same background (MacMicking, et al., "Altered Responses to Bacterial Infection and Endotoxic Shock in Mice Lacking Inducible Nitric Oxide Synthase [Published Erratum Appears in Cell Jun. 30, 1995; 81(7): Following 1170]," *Cell,* 81:641–50 (1995), which is hereby incorporated by reference). Similarly, wild type C57BL/6 mice were compared with phox91-deficient (respiratory burst oxidase-null) mice backcrossed to C57BL/6 (Pollock, et al., "Mouse Model of X-Linked Chronic Granulomatous Disease, an Inherited Defect in Phagocyte Superoxide Production," *Nat. Genet,* 9:202-9 (1995), which is hereby incorporated by reference). As expected, $H_2O_2$ product was preserved and NO production abolished in macrophages from NOS2-deficient mice, while the reverse was the case in macrophages from phox91-deficient mice; neither class of "knock-out" macrophages overproduced the opposite product. In all settings described below, results were similar with or without addition of exogenous IFN-γ to the already activated macrophages (not shown), and have been pooled.

Figure 7A:
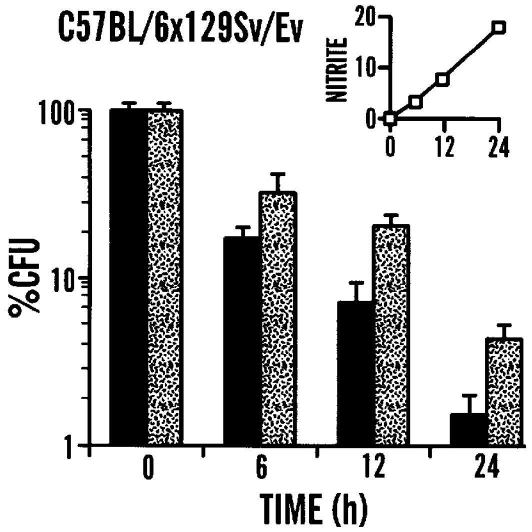
FIGS. 7A–D show the survival of NOXR1-transformed Mycobacterium smegmatis in wild type and genetically altered macrophages. Periodate-elicited peritoneal macrophages from wild type C57BL/6x129/SvEv (FIG. 6A), iNOS$^{-/-}$ C57LB/6x129/SvEv (FIG. 6B), wild type C57BL/6 (FIG. 6C), or phox91$^{-/-}$ C57BL/6 mice (FIG. 6D) were pretreated with mouse IFNγ and infected with Mycobacterium smegmatis transformed either with pOLYG (black bars) or with pOLYG-NO14 (gray bars). At indicated times, macrophages were lysed and surviving bacterial CFU determined. Values are means±SE for triplicate macrophage cultures as a percent of the starting CFU, defined as the CFU recoverable from the cells after the 30 min uptake period; the latter averaged $2\times10^5$ per well, or about 1 per macrophage. Insets: Nitrite accumulation (nmol/well) in the same cultures of macrophages infected with Mycobacterium smegmatis-pOLYG (squares) or pOLYG-NO14 (circles). Value are means±SE; error bars fall within the symbols. One of 6 similar experiments (3 with IFN-γ and 3 without).
Figure 7B:
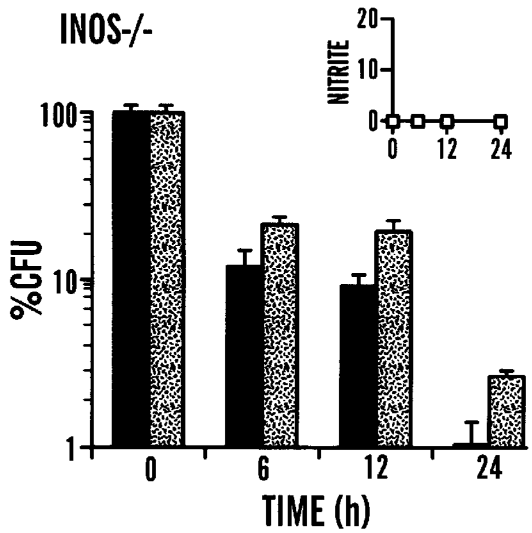
Figure 7C:
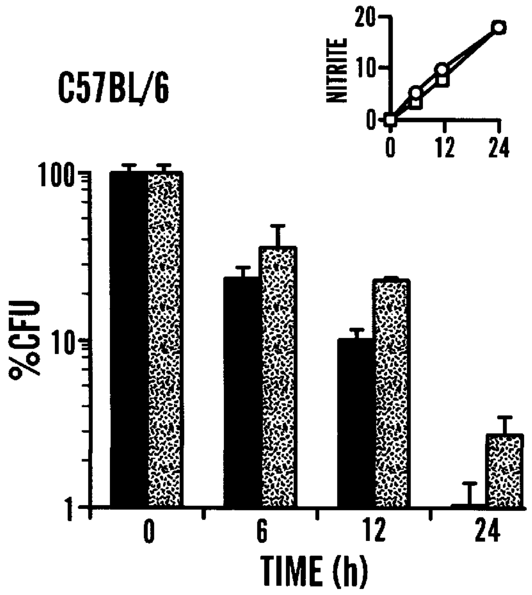

On average, activated macrophages from wild type C57BL/6x129/SvEv mice killed 80% of ingested pOLYG-transformed (control) *M. smegmatis* by 5.6 h and 97% by 24 h (FIG. 7A; interpolation from data in Table 1).

TABLE 1

Percent survival of vector- or NOXR1-transformed *M. smegmatis* after the indicated time periods compared to their cfu at time 0 in mouse macrophages

| Mouse Genotype | No. Exp. | Time (h) | Surviving vector-transformed *M. smegmatis*[1] (±SE) | Surviving NOXR1-transformed *M. smegmatis*[2] (±SE) | p-value[3] | Fold protection[4] (±SE) |
|---|---|---|---|---|---|---|
| C57BL/6x 129Sv/Ev | 6 | 6 | 14.2 (1.9) | 28.3 (3.7) | <.005 | 2.03 (0.21) |
| | | 12 | 9.7 (1.5) | 18.3 (2.5) | <.01 | 1.97 (0.21) |
| | | 24 | 2.8 (0.4) | 5.2 (0.3) | <.001 | 2.06 (0.29) |
| $iNOS^{-/-}$ | 6 | 6 | 19.0 (3.6) | 29.9 (5.3) | >.05 | 1.56 (0.08) |
| | | 12 | 14.0 (2.6) | 24.9 (4.5) | <.05 | 1.56 (0.14) |
| | | 24 | 4.1 (0.7) | 7.0 (1.0) | <.05 | 1.71 (0.20) |
| C57BL/6 | 6 | 6 | 32.1 (3.1) | 49.8 (3.8) | <.001 | 1.61 (0.16) |
| | | 12 | 21.0 (2.8) | 38.9 (4.1) | <.001 | 2.06 (0.14) |
| | | 24 | 6.7 (1.2) | 15.8 (2.8) | <.01 | 2.49 (0.33) |

TABLE 1-continued

Percent survival of vector- or NOXR1-transformed *M. smegmatis* after the indicated time periods compared to their cfu at time 0 in mouse macrophages

| Mouse Genotype | No. Exp. | Time (h) | Surviving vector-transformed *M. smegmatis*[1] (±SE) | Surviving NOXR1-transformed *M. smegmatis*[2] (±SE) | p-value[3] | Fold protection[4] (±SE) |
|---|---|---|---|---|---|---|
| Phox91-/- | 6 | 6 | 84.2 (9.1) | 110.0 (8.3) | <.05 | 1.42 (0.18) |
| | | 12 | 61.9 (4.7) | 96.4 (4.2) | <.0001 | 1.67 (0.20) |
| | | 24 | 22.0 (3.3) | 39.1 (3.7) | <.005 | 1.93 (0.27 |

[1,2]Means ± SE for the number of independent experiments indicated, each in triplicate. The number of CFU per well at time 0 was defined as 100%, and averaged $2 \times 10^5$, or approximately 1 per macrophage.
[1]*M. smegmatis* transformed with pOLYG vector alone.
[2]*M. smegmatis* transformed with pOLYG-NO14.
[3]Two-tailed Student's t-test.
[4]The percent surviving *M. smegmatis* pOLYG-NO14 divided by percent surviving *M. smegmatis* pOLYG at each time point was calculated for each experiment and averaged.

When *M. smegmatis* was transformed with NOXR1, it took the wild type macrophages 2-fold longer to kill 80% of them. Moreover, at each time point tested (6, 12, and 24 h), about 2-fold more bacteria survived (FIG. 7A; Table 1).

Macrophages genetically incapable of expressing NOS2 (MacMicking, et al., "Altered Responses to Bacterial Infection and Endotoxic Shock in Mice Lacking Inducible Nitric Oxide Synthase [Published Erratum Appears in Cell Jun. 30, 1995; 81(7): Following 1170]," *Cell,* 81:641–50 (1995), which is hereby incorporated by reference) were no less efficient at killing *M. smegmatis* than wild type macrophages of the same genetic background, with 80% killing by 6.0 h and 96% by 24 h (FIG. 7B; Table 1). This indicated that RNI are dispensable for the control of *M. smegmatis* in vitro, in contrast to the situation with *M. tuberculosis* (Chan, et al., "Killing of Virulent *Mycobacterium Tuberculosis* by Reactive Nitrogen Intermediates Produced by Activated Murine Macrophages," *J. Exp. Med.,* 175:1111–1122 (1992) and MacMicking, et al., "Altered Responses to Bacterial Infection and Endotoxic Shock in Mice Lacking Inducible Nitric Oxide Synthase [Published Erratum Appears in Cell Jun. 30, 1995; 81(7): Following 1170]," *Cell,* 81:641–50 (1995), and references cited therein, which are hereby incorporated by reference) and *M. leprae* (Adams et al., "L-Arginine-dependent Macrophage Effector Functions Inhibit Metabolic Activity of *Mycobacterium leprae*", *J. Immunol.,* 147:1642–1646 (1991), which is hereby incorporated by reference). Nonetheless, expression of NOXR1 protected the bacteria, delaying the time to 80% killing by a factor of 2.7-fold and resulting in 1.6- to 1.7-fold more surviving organisms at each time point tested (Table 1). This indicated that the protective action of NOXR1 is not directed exclusively against RNI, consistent with the in vitro showing that NOXR1 also protects against ROI.

Wild type C57BL/6 macrophages killed wild type (pOLYG-transformed) *M. smegmatis* more slowly than did wild type C57BL/6x129/SvEv macrophages (80% killing by 12.5 h). Nonetheless, expression of NOXR1 in *M. smegmatis* delayed the 80% killing time by a factor of 1.75-fold and resulted in 1.6- to 2.5-fold more surviving organisms at each time point tested (FIG. 7C; Table 1).

Figure 7D:
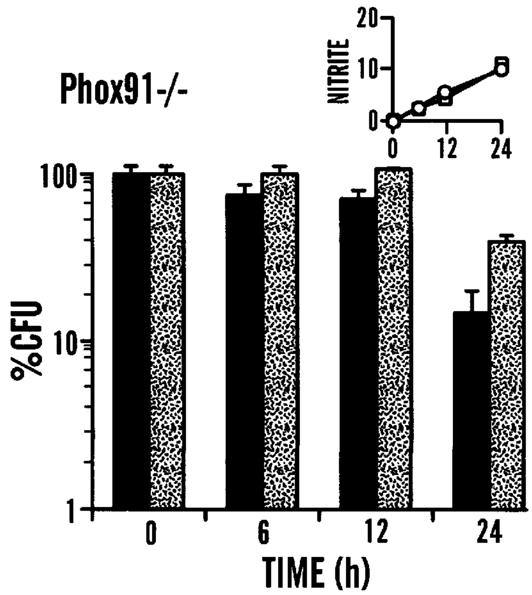

C57BL/6 macrophages deficient in phox91 were strikingly impaired in killing wild type *M. smegmatis*; within the 24 h period of observation, 80% killing was not often attained (FIG. 7D; Table 1). This indicated that ROI play a prominent, albeit not an exclusive role in killing *M. smegmatis*, in contrast to the situation with *M. tuberculosis*, where no role for ROI was evident (Chan, et al., "Killing of Virulent *Mycobacterium Tuberculosis* by Reactive Nitrogen Intermediates Produced by Activated Murine Macrophages," *J. Exp. Med.,* 175:1111–1122 (1992), which is hereby incorporated by reference). In ROI-deficient macrophages, *M. smegmatis* expressing NOXR1 survived 1.4- to 1.9-fold better than vector-transformed *M. smegmatis* at each time point tested (FIG. 7D; Table 1). These findings suggested that ROI and another product(s) represent redundant killing mechanisms for *M. smegmatis*, the former more effective than the latter; in the absence of ROI, less potent killing by RNI, $H^+$ or another product is manifest, against which NOXR1 affords protection.

This is the first study of macrophage-pathogen interactions in which both the macrophages and the pathogens have been genetically modified, such that the host cells do or do not express specific cytotoxic mechanisms, and the bacteria do or do not express a presumptive resistance pathway directed against those mechanisms. By this analysis, NOXR1, a novel gene from *M. tuberculosis*, confers partial resistance to three of the major antimicrobial products of macrophages, the cells ultimately responsible for controlling tuberculosis. The greater resistance conferred on NOXR1-transformed *M. smegmatis* in vitro than in macrophages strongly suggests there are macrophage antimycobacterial products other than RNI, ROI, and $H^+$, and that NOXR1 protects against some physiologically relevant stresses but not others.

Cloned from a prevalent clinical isolate of *M. tuberculosis*, NOXR1 was identified in the genome of all members of the *M. tuberculosis* complex except *M. microti*. NOXR1 was absent from the chromosome of mycobacteria considered nonpathogenic or opportunistically pathogenic for humans, including *M. smegmatis*. It is unknown if a NOXR1-like gene is present in any other organisms, nor whether NOXR1 is transcribed naturally by any mycobacteria besides the *M. tuberculosis* strain tested. It remains to be determined whether the natural gene may be regulated by environmental conditions, including the stresses against which it confers resistance. For example, NOXR1 might correspond to the NRI-induced protein of 14 kDa detected in *M. tuberculosis* by (Garbe, et al., "Response of *Mycobacterium Tuberculosis* to Reactive Oxygen and Nitrogen Intermediates," *Mol. Med.* 2, 134–142 (1996), which is hereby incorporated by reference). It would be of particular relevance to know how much NOXR1 is expressed by *M. tuberculosis* residing in phagolysosomes.

A major mystery is NOXR1's mechanism of action. With no homologies or motifs recognized at nucleotide or amino acid levels, the sequence afforded few clues. Because so little NOXR1 appears to be expressed, it is unlikely that its four cysteine residues merely serve to titrate ROI or RNI, as homocysteine is thought to do in *Salmonella typhimurium* (De Groote et al., "NO Inhibitions: Antimicrobial Properties of Nitric Oxide," *Clin. Infect. Dis.,* 21:162–165 (1996), which is hereby incorporated by reference), or as metallothionein may do when overexpressed in hepatocytes (Schwarz, et al., "Metallothionein Protects Against the Cytotoxic and DNA-Damaging Effects of Nitric Oxide," *Proc. Natl. Acad. Sci, U.S.A* 92:4452–4456 (1995), which is hereby incorporated by reference). NOXR1 may work instead as a DNA-binding protein, a possibility raised by its basicity. In *E. coli*, the DNA-binding protein encoded by dps protects DNA from oxidative damage (Almiron, et al., "A Novel DNA-Binding Protein With Regulatory and Protective Roles in Starved *Escherichia coli,*" *Genes Dev.,* 6:2646-54 (1992) and Altuvia, et al., "The dps Promoter is Activated by OxyR During Growth and by IHF and Sigma S in Stationary Phase," *Mol. Microbiol.,* 13:265-72 (1994), which are hereby incorporated by reference), and NOXR1 might work in a similar manner. Its effectiveness in a heterologous mycobacterium from whose own genome it is lacking may argue against a role as a transcription factor, and its effectiveness in OxyR- and SoxRS-deficient *E. coli* argues against NOXR1 activating those two regulons in particular. The OxyR homolog of *M. tuberculosis* contains numerous deletions and frameshifts and is nonfunctional (Deretic, et al., "*Mycobacterium Tuberculosis* is a Natural Mutant With an Inactivated Oxidative-Stress Regulatory Gene: Implications For Sensitivity to Isoniazid,"*Mol. Microbiol.,* 17:889–900 (1995) and Sherman, et al., "Disparate Responses to Oxidative Stress in Saprophytic and Pathogenic Mycobacteria," *Proc. Natl. Acad. Sci. USA,* 92:6625-9 (1995), which are hereby incorporated by reference). Perhaps NOXR1 compensates for the loss of OxyR in *M. tuberculosis* similar to the suggested role of AhpC (Dhandayuthapani, et al., "Oxidative Stress Response and Its Role in Sensitivity to Isoniazid in Mycobacteria: Characterization and Inducibility of ahpC by Peroxides in *Mycobacterium Smegmatis* and Lack of Expression in *M. Aurum* and *M. Tuberculosis,*" *J. Bacteriol,* 178:3641-9 (1996) and Sherman, et al., "Compensatory ahpC Gene Expression in Isoniazid-Resistant *Mycobacterium Tuberculosis,*" *Science,* 272:1641-3 (1996), which are hereby incorporated by reference).

If NOXR1 is an enzyme, the novelty of its sequence suggests that it may work differently than those already known to affect RNI. The latter serves to alter the proportions of various RNI in a mixture. Thus, in vitro, mammalian thioredoxin reductase can catalyze the NADPH-dependent reduction of S-nitrosoglutathione to GSH and an NO-like species (Nikitovic, et al., "S-Nitrosogluthathione is Cleaved by Thioredoxin System With Liberation of Glutathion and Redox Regulating Nitric Oxide," *J. Biol. Chem.,* 271:19180–19185 (1996), which is hereby incorporated by reference), while superoxide dismutase favors the accumulation of NO at the expense of its conversion to peroxynitrite. At present, the yield of recombinant NOXR1 has been compromised by its apparent autotoxicity upon overexpression, and this has precluded biochemical assays of hypothesized actions.

The physiologic role of NOXR1 cannot be established until it is possible to inactivate NOXR1 selectivity in *M. tuberculosis* and compare the growth of the organism in the mammalian host with the growth of isogenic *M. tuberculosis* to which NOXR1 has been restored. Until then, the possibility remains that the actions of NOXR1 observed in transformed bacteria are artefacts of over- or heterologous expression. Weighing against this concern is that NOXR1 conferred a protective phenotype only when expressed at low levels, and did so in diverse species and strains.

There is urgent need for new antitubercular drugs. Almost all currently used antibacterials manifest their antibacterial activity in pure culture, and new candidates are screened on that basis. Such screens could miss compounds that inhibit a pathway which is dispensable for bacterial growth in vitro but which confers a survival advantage on the pathogen within the infected host. In this sense, inhibitors of NOXR1 may warrant investigation as possible prototypes of a new class of anti-infectious agents.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated protein or polypeptide encoded by a DNA molecule conferring on *Mycobacterium tuberculosis* resistance to antimicrobial reactive oxygen and reactive nitrogen intermediates.

2. An isolated protein or polypeptide according to claim 1, wherein the protein or polypeptide has an amino acid sequence comprising SEQ. ID. No. 2.

3. An isolated protein or polypeptide according to claim 2, wherein said DNA molecule comprises a nucleotide sequence of SEQ. ID. No. 1.

4. An isolated protein or polypeptide according to claim 1, wherein said protein or polypeptide is recombinant.

5. An isolated protein or polypeptide according to claim 1, wherein said protein or polypeptide is purified.

6. An isolated protein or polypeptide according to claim 1, wherein said protein or polypeptide has one or more antigenic determinants conferring on *Mycobacterium tuberculosis* resistance to antimicrobial reactive oxygen and nitrogen intermediates.

7. A pharmaceutical composition comprising:

an isolated protein or polypeptide according to claim 1, and a pharmaceutically-acceptable carrier.

8. A pharmaceutical composition according to claim 7, wherein said protein or polypeptide is purified.

9. An isolated protein or polypeptide comprising amino acid sequence SEQ. ID. NO. 4.

* * * * *

UNITED STATES PATENT AND TRADEMARK OFFICE

CERTIFICATE OF CORRECTION

PATENT NO. : 6,177,086 B1

APPLICATION NO. : 09/067626

DATED : January 23, 2001

INVENTOR(S) : Lee W. Riley

It is certified that error appears in the above-identified patent and that said Letters Patent is hereby corrected as shown below:

Col. 1 at lines 9-12, delete "This invention arose out of research sponsored by the National Institutes of Health (Grant No. RO1-HL51967-01). The U.S. Government may have certain rights in this invention." and insert --This invention was made with government support under grant RO1-HL51967-01 awarded by National Institutes of Health. The government has certain rights in the invention-- in its place.

Signed and Sealed this

Twenty-fourth Day of February, 2009

JOHN DOLL

*Acting Director of the United States Patent and Trademark Office*